(12) United States Patent
Mineau-Hanschke

(10) Patent No.: US 6,419,920 B1
(45) Date of Patent: *Jul. 16, 2002

(54) HYBRID MATRIX IMPLANTS AND EXPLANTS

(75) Inventor: Rochelle Mineau-Hanschke, Andover, MA (US)

(73) Assignee: Trans Karyotic Therapies, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/413,715

(22) Filed: Oct. 5, 1999

Related U.S. Application Data

(60) Continuation-in-part of application No. 09/312,246, filed on May 14, 1999, which is a division of application No. 08/548,002, filed on Oct. 25, 1995, now Pat. No. 5,965,125.

(51) Int. Cl.$^7$ .................. A01N 63/00; A61F 13/00; C12N 5/00; A61K 48/00

(52) U.S. Cl. .................. 424/93.21; 424/422; 435/382; 435/325; 435/320.1; 435/455

(58) Field of Search .................. 424/93.21, 422; 435/455, 320.1, 69.1, 69.3, 69.52, 382, 325

(56) References Cited

U.S. PATENT DOCUMENTS

| | | | |
|---|---|---|---|
| 4,485,096 A | 11/1984 | Bell | 424/532 |
| 4,604,346 A | 8/1986 | Bell et al. | 606/132 |
| 4,686,098 A | 8/1987 | Kopchick et al. | 424/424 |
| 4,837,379 A | 6/1989 | Weinberg | 424/548 |
| 4,861,714 A | 8/1989 | Dean, Jr. et al. | 435/69.1 |
| 4,863,856 A | 9/1989 | Dean, Jr. et al. | 435/69.1 |
| 4,963,489 A | 10/1990 | Naughton et al. | 435/240.1 |
| 4,997,753 A | 3/1991 | Dean, Jr. et al. | 435/69.1 |
| 5,032,508 A | 7/1991 | Naughton et al. | 435/32 |
| 5,100,783 A | 3/1992 | Dean, Jr. et al. | 435/69.1 |
| 5,266,480 A | 11/1993 | Naughton et al. | 435/240.243 |
| 5,270,192 A | 12/1993 | Li et al. | 435/174 |
| 5,762,926 A * | 6/1998 | Gage et al. | 424/93.21 |
| 5,906,817 A | 5/1999 | Mouiller et al. | 424/93.21 |

FOREIGN PATENT DOCUMENTS

| | | |
|---|---|---|
| EP | 0 344 924 A2 | 12/1989 |
| EP | 0 361 957 A1 | 4/1990 |
| EP | 0 418 035 A1 | 3/1991 |
| EP | 0 419 111 A1 | 3/1991 |
| EP | 0 457 430 A2 | 11/1991 |
| FR | 2 704 236 | 10/1994 |
| FR | 2 708 202 | 2/1995 |
| WO | WO 80/01350 | 7/1980 |
| WO | WO 93/09222 | 5/1993 |
| WO | WO 93/09222 A1 | 5/1993 |
| WO | WO 94/10950 A1 | 5/1994 |
| WO | WO 94/12650 | 6/1994 |
| WO | WO 94/24298 | 10/1994 |
| WO | WO 95/19430 | 7/1995 |
| WO | WO 97/15195 | 5/1997 |

OTHER PUBLICATIONS

Wivel et. al.; Methods of Gene Delivery, 1998, Hematology/Oncology Clinics of North America vol. 12, No. 3: 483–501.*

Kohn; Gene therapy for haematopoietic and lymphoid disorders, 1997, Clin. Exp. Immunoi 107: 54–57.*

Riddell et al.; T–Cell mediated rejection of gene–modified HIV–specific cytotoxic T lymphocytes in HIV–infected patients, 1996, Nature Medicine, vol. 2 No. 2:216–223.*

St. Louis et al. An alternative approach to somatic cell gene therapy. (1988) Proc. Natl. Acad. Sci. USA 85:3150–3154.

Nilsson et al., "Growth of Anchorage–Dependent Cells on Macroporous Microcarriers," Bio/Technology 4:989–990, 1986.

Bell et al., Production of a Tissue–like structure by Contraction of Collagen Lattices by Human Fibroblast of Different Proliferative Potential In Vitro, Proc. Natl. Acad. Sci. USA 76:1274–1278, 1979.

Bell et al., Recipes for Reconstituting Skin, J. Biomechanical Engineering 113:113–119, 1991.

Bergsteindottir et al., The Effect of Three Dimensional Collagen Type I Preparation on the Structural Organization of Guinea Pig Enteric Ganglia in Culture, Experimental Cell Research 209:64–75, 1983.

Bisbee et al., Mouse Mammary Epithelial Cells on Floating Collagen Gels: Transepithelial Ion Transport and Effects of Prolactin, Proc. Natl. Acad. Sci. USA 76:536–540, 1979.

Boyce et al., Biologic Attachment, Growth, and Differentiation of Cultured Human Epidermal Keratinocytes a Graftable Collagen and Chondroitin–6–Sulfate Substrate, Surgery 103:421–430, 1988.

Demetriou et al., Replacement of Liver Function in Rats by Transplantation of Microcarrier–Attached Hepatocytes, Science 233:1190–1192, 1986.

Elsdale and Bard, Collagen Substrate for Studies on Cell Behavior, J. Cell Biology 54:626–627, 1972.

Emerman and Pitelka, Maintenance and Induction of Morphological Differentiation in Dissociated Mammary Epithelium on Floating collagen Membranes, In Vitro 13:316–328, 1977.

Gilbert et al., Cell Transplantation of Genetically Altered Cells on Biodegradable Polymer Scaffolds in Syngeneic Rats, Transplantation 56:423–427, 1993.

(List continued on next page.)

Primary Examiner—Dave T. Nguyen
Assistant Examiner—Quang Nguyen
(74) Attorney, Agent, or Firm—Fish & Richardson P.C.

(57) ABSTRACT

A composition having a body of matrix material made up of insoluble collagen fibrils, and disposed therewithin (a) a plurality of vertebrate cells;

(b) a plurality of microspheres; and (c) an agent such as a factor that promotes vascularization, a cytokine, a growth factor, or ascorbic acid.

66 Claims, 9 Drawing Sheets

OTHER PUBLICATIONS

Halberstadt et al., The In Vitro Growth of a Three–Dimensional Human Dermal Replacement Using a Single–Pa Perfusion System, Biotechnology and Bioengineering 43:740–746, 1994.

Kleinman et al., Role of Collagenous Matrices in the Adhesion and Growth of Cells, J. Cell Biology 88:473–485, 1981.

Krueger et al., Genetically Modified Skin to Treat Disease: Potential and Limitations, J. Investigative Dermatology, 103:76S–84S, 1994.

Moullier et al., Long–term Delivery of a Lysosomal Enzyme by Genetically Modified Fibroblasts in Dogs, Nature Medicine, 1: 353–357, 1995.

Moullier et al., Correction of Lysosomal Storage in the Liver and Spleen of MPS VII Mice by Implantation of Genetically Modified Skin Fibroblasts, Nature Genetics 4:154:159, 1993.

Moullier et al., Continuous Systemic Secretion of a Lysosomal Enzyme by Genetically Modified Mouse Skin Fibroblasts, Transplantation 56:427–432, 1993.

Nakagawa et al., Long–term Culture of Fibroblasts in Contracted Collagen Gels: Effects on Cells Growth and Biosynthetic Activity, J. Investigative Dermatology 93:792–798, 1989.

Palmer et al., Genetically Modified Skin Fibroblasts Persist Long After Transplantation but Gradually Inactivate Introduced Genes, Proc. Natl. Acad. Sci. USA 88:1330–1334, 1991.

Palmer et al., Production of Human Factor IX in Animals by Genetically Modified Skin Fibroblasts: Potent Therapy for Hemophilia B, Blood 73:438–445, 1989.

Reuveny, Microcarriers in Cell Culture: Structure and Applications, Advances in Cell Culture 4:213–47, 1985.

Shahar et al., Cerebral Neurons, Skeletal Myoblasts, and Cardiac Muscle Cells Cultured on Macroporous Beds Biotechnology and Bioengineering 43:826–831, 1994.

Turley et al., The Retention and Ultrastructural Appearances of Various Extracellular Matrix Molecules Incorporated into Three–Dimensional Hydrated Collagen Lattices, Developmental Biology 109:347–369, 1985.

Varani et al., Cell Growth on Microcarriers: Comparison of Proliferation on and Recovery from Various Substrates J. Biological Standardization 14:331–336, 1986.

Vournakis and Runstadler, Microenvironment: The Key to Improved Cell Culture Products, Bio/Technology 7:143–145, 1989.

Weinberg and Bell, Regulation of Proliferation of Bovine Aortic Endothelial Cells, Smooth Muscle Cells, Adventitial Fibroblasts in Collagen Lattices, J. Cellular Physiology 122:410–414, 1985.

Sullivan et al., "Biohybrid Artificial Pancreas: Long–Term Implantation Studies on Diabetic, Pancreatectomized Dogs," Science 252:718–721, May 3, 1991.

Bartlett et al., "Regulation of neural stem cell differentiation in the forebrain," Immunol. Cell. Biol. 76(5):414–418, 1998 (Abstract only).

Chen et al., "Differential roles for bone morphogenic protein (BMP) receptor type IB and IA differentiation and specification of mesenchymal . . . lineages," J. Cell. Biol. 142(1):295–305, 1998 (Abstract only).

Freshney, (ed.), Culture of Human Cells, 3rd Edition, Wiley– Liss, Inc., 1994, pp. 219–224.

Gregoire et al., "Understanding adipocyte differentiation," Physiol. Rev. 78(3):783–809, 1998 (Abstract only).

Hansbrough et al., "Evaluation of a biodegradable matrix containing cultured human fibroblasts as a dermal replacement beneath meshed skin grafts on athymic mice," Surgery, 11:438–446, 1992.

Nakajima et al., "Adipose tissue extracellular matrix: newly organized by adipocytes during differentiation," Differentiation 63(4):193–200, 1998 (Abstract only).

Wilkens et al., "Development of a bilayerd living skin construct for clinical applications," Biotech. Biogen. 43:747–756, 1994.

Product Description for Unweighted Macroporous Microspheres, "Cellex Biosciences Technical Note," Cellex Biosciences, Inc., 10 pages, 1994.

Product Description for Verax® microspheres, "Verax VX–100® Microspheres Technical Specifications," Verax® Corporation, 2 pages, 1991.

Black et al., "In vitro reconstruction of a human capillary–like network in a tissue–engineered skin equivalent," FASEB J. 12:1331–1340, 1998.

Black et al., "A novel approach for studying angiogenesis: A human skin equivalent with a capillary–like network," Cell Biology and Toxicology 15:81–90, 1999.

Bell et al., "Recipes for Reconstituting Skin," J. of Biomechanical Engineering 113:113–119, 1991.

DeBlois et al., "Heparin–fibroblast growth factor–fibrin complex . . . materials," Biomaterials 15(9):665–672, 1994.

Descamps et al., "Organoids direct systemic expression of erythropoietin in mice," Gene Therapy 2:411–417, 1995.

Hayek et al., "Angiogenic Peptides in Pancreatic Islet Transplantation to Diabetic Rats," Transplantation 50(6): 931–933, 1990.

Mooney et al., "Localized Delivery of Epidermal Growth Factor Improves the Survival of Transplanted Hepatocytes," Biotechnology and Bioengineering 50:422–429, 1996.

Parenteau et al., "Epidermis Generated In Vitro: Practical Considerations and Applications," J. of Cellular Biochemistry 45:245–251, 1991.

Watanabe et al., "Effect of basic fibroblast growth factor on angiogenesis in the infracted porcine heart," Basic Res. Cardiol. 93:30–37, 1998.

Zarge et al., "Fibrin glue containing fibroblast growth factor type 1 . . . model," J Vasc Surg 25:840–9, 1997.

* cited by examiner

HYBRID MATRIX IMPLANTS AND EXPLANTS

This application is a continuation-in-part of application number 09/312,246, filed May 14, 1999, which is a divisional application of application number 08/548,002, filed Oct. 25, 1995 now U.S. Pat. No. 5,965,125.

The field of the invention is medical devices used in vivo or in vitro for production and delivery of medically useful substances.

BACKGROUND OF THE INVENTION

The means used to deliver medically useful substances can significantly affect their efficacy. The standard route of administration for many such substances is either oral, intravenous, or subcutaneous. Each has inherent limitations which can affect the therapeutic utility of the substances being delivered. Furthermore, many protein-based drugs have short half-lives and low bioavailabilities, factors that must be considered in their formulation and delivery. Although various devices have been developed to deliver medically useful substances, including portable pumps and catheters, there is still a significant need for improved delivery devices.

Many medically useful substances, including proteins, glycoproteins, and some peptide and nonpeptide hormones, are more efficiently produced by cultured cells than via artificial synthetic routes. Appropriate cells are typically cultured in bioreactors, and the desired product purified therefrom for administration to the patient by standard means, e.g. orally or by intravenous or subcutaneous injection. Alternatively, the cells may be implanted directly into the patient, where they produce,and deliver the desired product (see, e.g., U.S. application Ser. Nos. 07/787,840 and 07/789,188). While this method has a number of theoretical advantages over injection of the product itself, including the possibility that normal cellular feedback mechanisms may be harnessed to allow the delivery of physiologically appropriate levels of the product, it introduces additional complexities. One of these concerns the appropriate environment for the cells at the time of implantation. It would be desirable to organize the cells of the implant in a form that is compatible with the natural in vivo environment of the cell type comprising the implant (fibroblasts, for example, exist naturally in a rich network of extracellular matrix composed primarily of collagen). There is also a need in some cases to ensure that the implanted cells remain localized to a defined site in the patient's body, so that they can be monitored and perhaps removed when no longer needed.

One technique that has been tested for this purpose utilizes an implantation device consisting of a solid, unitary piece of collagen gel (a "collagen matrix") in which the cells are embedded (e.g., Bell, U.S. Pat. No. 4,485,096). Other substances, such as polytetrafluoro-ethylene (PTFE) fibers (Moullier et al., Nature Genetics, 4:154, 1993; WO 94/24298), may be included in the collagen implant to impart strength or other desirable characteristics to the collagen gel.

SUMMARY OF THE INVENTION

It has been found that the function of collagen matrices can be substantially improved by the addition of microspheres (i.e., microcarriers of any shape) to the collagen matrix, thereby forming what is herein termed a "hybrid matrix". This may be accomplished by mixing microspheres with the cells and soluble collagen prior to gelling of the collagen to form the matrix. If desired, the microspheres and cells can be cultured together for a period which permits the cells to adhere to the microspheres before addition of the non-gelled collagen solution; alternatively, the three constituents can be mixed essentially simultaneously or in any desired order, followed by gelation of the soluble collagen within the mixture, to form a gelled mixture consisting of insoluble collagen fibrils, cells and microspheres. This gelled mixture gradually becomes smaller through the exclusion of liquid to form a solid, relatively resilient, implantable unit that contains both the microspheres and the cells embedded in the insoluble collagen fibril network. When the microspheres are also composed largely of collagen, the resulting matrix is herein termed a "hybrid collagen matrix". It is understood that the microspheres in the hybrid collagen matrices could contain substances in addition to collagen.

The invention thus includes an article, composition, or device having a body made of matrix material that includes insoluble collagen fibrils, and disposed within the body:
  (a) a plurality of vertebrate cells (particularly mammalian cells such as cells derived from a human, chimpanzee, mouse, rat, hamster, guinea pig, rabbit, cow, horse, pig, goat, sheep, dog, or cat); and
  (b) a plurality of microspheres, each of which preferably consists primarily of (i.e., greater than 50% of its dry weight is) one or more substances selected from a list including collagen (preferably type I collagen), polystyrene, dextran, polyacrylamide, cellulose, calcium alginate, latex, polysulfone, glass (e.g., glass coated with a gel such as collagen, to improve adherence of cells), and gelatin (e.g., porous gelatin). Generally at least 70%, and preferably at least 80% (most preferably between approximately 90% and approximately 100%, e.g., at least 95%) of each microsphere's dry weight is one or more of the listed substances. Commercial examples of microspheres which are described as consisting essentially of purified collagen include ICN Cellagen™ Beads and Cellex Biosciences macroporous microspheres. The microspheres are preferably of a porous consistency, but may be smooth, and typically have an approximately spherical shape with a diameter of approximately 0.1 to 2 mm (e.g., between approximately 0.3 and 1 mm). Of course, the shape and size of microspheres from any particular lot or preparation will vary within manufacturing tolerances.

The article may be configured to be implanted into an animal, e.g., a mammal such as a human patient, or may be designed for producing cellular products in vitro; e.g., in an extracorporeal bioreactor apparatus having a means for shunting blood from an animal to the article and then back into a blood vessel of the animal, or in a bioreactor or other vessel from which medium containing the desired cellular product can be recovered for purification and the preparation of a pharmaceutical agent.

The cells may be derived from one or more cells removed from the patient, and preferably are genetically engineered (e.g., transfected) cells containing exogenous DNA encoding one or more medically useful polypeptides such as an enzyme, hormone, cytokine, colony stimulating factor, angiogenesis factor, vaccine antigen, antibody, clotting factor, regulatory protein, transcription factor, receptor, or structural protein. Examples of such polypeptides include human growth hormone (hGH), Factor VIII, Factor IX, erythropoietin (EPO), albumin, hemoglobin, alpha-1 antitrypsin, calcitonin, glucocerebrosidase, low density lipoprotein (LDL) receptor, IL-2 receptor, globins, immunoglobulins, catalytic antibodies, the interleukins, insulin, insulin-like growth factor 1 (IGF-1), insulinotropin, parathyroid hormone (PTH), leptin, an interferon (IFN) (e.g., IFNα, IFNβ, or IFN-γ), nerve growth factors, basic fibroblast growth factor (bFGF), acidic FGF (aFGF), epidermal growth factor (EGF), endothelial cell growth factor, platelet derived growth factor (PDGF), transforming growth factors, endothelial cell stimulating angiogenesis factor (ESAF), angiogenin, tissue plasminogen activator (t-PA), granulocyte colony stimulating factor (G-CSF), granulocyte-macrophage colony stimulating factor (GM-CSF), follicle stimulating hormone (FSH), α-galactosidase, β-gluceramidase, α-iduronidase, α-L-iduronidase, glucosamine-N-sulfatase, α-N-acetylglucosaminidase, acetylcoenzyme A:α-glucosaminide-N-acetyltransferase, N-acetylglucosamine-6-sulfatase, β-galactosidase, N-acetylgalactosamine-6-sulfatase, and β-glucuronidase. Alternatively, the exogenous DNA can contain a regulatory sequence, and optionally other elements, that will activate expression of an endogenous gene (for example, using homologous recombination as described in WO94/12650-PCT/US93/11704, which is incorporated by reference herein).

Generally any type of cell which is capable of attaching to collagen and/or the microspheres, and which exhibits a desirable property such as expression of a medically useful cellular product or performance of an essential structural or metabolic function, can be utilized in the matrices of the invention. Examples include adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, pancreatic beta cells, renal cells, smooth muscle cells and striated muscle cells, as well as precursors of any of the above. If desired, more than one type of cell can be included in a given matrix. The cells may be present as clonal or heterogenous populations.

The collagen in the matrix material is preferably type I, but may be any other type of collagen. The matrix material may optionally include two or more types of collagen (e.g., selected from types I, II, III, IV, V, VI, VII, VIII, IX, X, and XI), as well as any additional components that impart desirable characteristics to the resulting matrix: e.g., agarose, alginate, fibronectin, laminin, hyaluronic acid, heparan sulfate, dermatan sulfate, chondroitin sulfate, sulfated proteoglycans, fibrin, elastin, tenascin, heparin or polysaccharides such as cellulose, starch or dextran. Any of the above mentioned collagenous and non-collagenous components may be derived from human sources or from another animal source. One could also include collagen or non-collagen fibers disposed within the device. Collagen fibers can be in the form of cross-linked collagen threads dispersed within the body of the matrix material. Non-collagen fibers can, for example, be made of a material that includes nylon, dacron, polytetrafluoro-ethylene, polyglycolic acid, polylactic/polyglycolic acid polymer mixtures, polystyrene, polyvinylchloride co-polymer, cat gut, cotton, linen, polyester, or silk.

Large numbers of cells can be contained within the hybrid matrices. For example, hybrid matrices can be prepared which contain at least approximately two (and preferably approximately three) times as many cells as matrices prepared with soluble collagen alone, assuming the number of cells inoculated and the initial production volume are equivalent. The total amount of polypeptide expressed by the cells embedded in a given hybrid matrix in a given time period is typically significantly higher (e.g., at least 50% higher, preferably at least 100% higher, and more preferably at least 200% higher) than achieved with a standard collagen matrix prepared from an equivalent volume of starting material.

Any of the above-described hybrid matrices of the invention can also contain one or more (e.g., at least 2, 3, 4, 5, 6, 8, or 10) agents intended to improve the functioning of the matrix, e.g., by increasing proliferation and/or maintenance of the cells. These agents can include, for example, factors which promote vascularization, cytokines, or growth factors. While the agent used in a particular hybrid matrix and the polypeptide, e.g., a medically useful polypeptide, produced by the cells in the matrix can be the same substance, the two entities will generally be different. The agent can be added directly to the mixture used to make the hybrid matrices or can be bound to or encapsulated within a solid substrate which is added to the same mixture. The solid substrate can be the microspheres themselves or can be a separate entity or entities (e.g., multiple particles of the solid substrate, or a single piece, embedded in the matrix. The solid substrate can have heparin or heparan sulfate proteoglycan bound to it, as a means for promoting binding of the agent. An example of such a solid substrate is one that consists primarily of agarose (e.g., Sepharose™, Affi-Gel™ Heparin Gel, or Heparin-agarose), with or without heparin or heparan sulfate proteoglycan bound to it; such a solid substrate can also contain calcium alginate. Other substances from which the solid substrates can be manufactured include collagen, gelatin, ethylene-vinyl acetate, polylactide/glycolic acid co-polymer, fibrin, sucrose octasulfate, dextran, polyethylene glycol, an alginate, polyacrylamide, cellulose, latex, polyhydroxyethylmethacrylate, nylon, dacron, polytetrafluoro-ethylene, polyglycolic acid, polylactic acid, polystyrene, polyvinylchloride co-polymer, cat gut, cotton, linen, polyester, and silk. The solid substrate can be in a variety of physical forms, e.g., beads, irregular particles, sheets, or threads. When the agent is encapsulated in the solid substrate, the agent is released gradually over time, e.g., due to enzymes that act on the solid substrate.

Examples of agents which can be used in the matrices include basic fibroblast growth factor (bFGF), vascular endothelial growth factor (VEGF), VEGF-A, VEGF-B, VEGF-C, VEGF-D, acidic fibroblast growth factor (aFGF), endothelial cell growth factor, platelet-derived growth factor (PDGF), endothelial cell stimulating angiogenesis factor (ESAF), leukotriene $C_4$, a prostaglandin, insulin-like growth factor 1 (IGF-1), granulocyte colony stimulating factor (G-CSF), angiogenin, transforming growth factor-α (TGF-α), transforming growth factor-β (TGF-β), ascorbic acid, epidermal growth factor (EGF), or oncostatin M.

The bioactive concentration of each agent will vary greatly. A starting range is provided by the manufacturer and is usually based on a standard bioactivity assay using, for example, degree of cell proliferation as the end point. Typically, the agent is bound at a broad range of concentrations (lowest being what is reported as bioactive by the vendor, highest being as much as 1000× that of the reported concentration) to a substrate such as heparin-Sepharose beads; the beads are incorporated into an HCM; and the release of the agent over time in vitro is monitored using an appropriate detection system (e.g., an immunoassay). For these release assays, the matrices are placed in growth medium containing 10% serum. Once it is determined that the matrices release detectable amounts of the agent, a bioactivity assay is performed. Matrices containing a range of agent concentrations can, for example, be placed on porous inserts (3 to 8 μm pores) above cells that are known to proliferate in response to the agent (e.g, endothelial cells for VEGF and bFGF, fibroblasts for bFGF and PDGF, as indicated by manufacturer), and cell growth curves determined. The results of the in vitro bioactivity assay are evaluated and doses that are not deemed bioactive as well as doses that are determined to be "toxic" (i.e., lead to cell numbers lower than control) are noted. In order to determine the optimal concentration of agent per matrix, matrices containing the agent at a range of concentrations based on the in vitro bioactivity results are implanted in immunocompromised mice. The optimal agent concentration per matrix is typically the concentration that allows for the maximum amount of therapeutic protein to be released for the maximum amount of time in vivo.

Instead of (or in addition to) the described agent per se being dispersed in the body of the matrix material, the hybrid matrices can contain, in addition to the first population of cultured vertebrate cells genetically engineered to express a polypeptide (e.g., a medically useful polypeptide), a second population of cultured vertebrate cells expressing and secreting one or more (e.g., at least 2, 3, 4, 6, 8, or 10) of the agents. The cultured vertebrate cells of the second population can be genetically engineered (as described below) to express the agent, or can be a cell which produces the agent without the benefit of genetic engineering. In the latter case, if the cell does not constitutively produce the polypeptide, or produces it in very low amounts, the cell can be induced to produce the agent, or produce it higher amounts by gene activation. The first and second populations can be the same population of cells transfected with a DNA encoding the polypeptide and a DNA encoding the agent (or encoding the enzyme(s) necessary to produce the agent, such as for ascorbic acid); alternatively, the cells can be transfected with a single DNA encoding both the polypeptide and the agent or agent-producing enzyme(s). The matrices of the invention can contain additional populations of cultured vertebrate cells which express and secrete additional examples of the above described agents. The cultured vertebrate cells of the agent-producing populations can be adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, pancreatic beta cells, renal cells, smooth muscle cells, striated muscle cells, or precursors of any of the above. The cells are preferably human cells, but can be cells of any vertebrate (e.g., a mammal such as a non-human primate, pig, cow, horse, goat, sheep, dog, cat, mouse, rat, rabbit, guinea pig or hamster). When cells producing the agent are included in the matrix, one can optionally include the solid substrate as well, to bind a portion of the agent as it is secreted from the cells. This provides a means for controlling the rate of release of the agent from the hybrid matrix.

In one preferred embodiment, the hybrid matrices of the invention contain keratinocytes, e.g., (a) as the cells which produce the polypeptide, (b) as the cells which produce the agent, (c) both (a) and (b), or (d) as a population which produces neither the polypeptide nor the agent. Hybrid matrices to which the keratinocytes are added are preferably those containing fibroblasts as cells producing the above-described polypeptide (e.g., a medically useful polypeptide) and/or agent. The keratinocytes and the fibroblasts can be obtained from the same individual, and one or more keratinocyte differentiation factors (e.g., calcium ions at a concentration of 1.5–2 mM, TGF-β, or keratinocyte differentiation factor-1 (KDF-1)) can be added to the hybrid matrix.

In a similar manner, the hybrid matrices of the invention may contain endothelial cells, preferably in addition to fibroblasts producing a medically useful polypeptide, and even in addition to both fibroblasts and keratinocytes. The endothelial cells and fibroblasts can be obtained from the same individual. One or more endothelial differentiation factors (e.g. vascular endothelial growth factor or basic fibroblast growth factor at 10 ng–10 μg) can be added to the hybrid matrix to induce the formation of endothelial tubes within the matrix. The growth factors can be added directly to the matrix during formation, or added to the matrix growth medium, or both.

The hybrid matrix of the invention is generally prepared by a process that includes the following steps:

forming a mixture that includes (a) a plurality of vertebrate cells; (b) a plurality of microspheres, each of which preferably consists primarily of one or more substances selected from the list consisting of collagen, polystyrene, dextran, polyacrylamide, cellulose, calcium alginate, latex, polysulfone, and glass; and (c) a solution comprising soluble collagen;

causing the soluble collagen in the mixture to form a gel of insoluble collagen fibrils in which the cells and the microspheres are embedded; and exposing the gel to culture conditions which cause the gel to become smaller by the exclusion of liquid, thereby forming the body of the article. Gelation is typically triggered by raising the pH of the relatively acidic collagen solution to above 5, e.g., by addition of concentrated, buffered culture medium, whereupon the collagen forms insoluble fibrils. When this step is carried out in a mold, the gel will take the shape of the interior of the mold. Generally the contraction of the gel is effected by the cells in the mixture, which attach to the fibrils and cause the gel to contract to a smaller version of the molded shape (e.g., a disk, as in the case where the mold is a petri dish which is cylindrical in shape). The matrix may be utilized immediately after manufacture, may be cultured to increase the number of cells present in the matrix or to improve their functioning, or may be cryopreserved indefinitely at a temperature below 0° C. They can also be stored temporarily in a higher temperature refrigerator at, for example, about 4° C.

For making those hybrid matrices containing one or more of the above-described agents, the relevant agents (free or bound to any of the above-described solid substrates) are added, together with the other components listed above, to the mixture. The agent and solid substrate can be added to the mixture together or separately, in any order. Additionally or alternatively, the mixture can contain a second (and, optionally, a third, fourth, fifth, sixth, or more) population of cultured vertebrate cells secreting one or more of the described agents. The mixture can also contain one or more of the above-described solid substrates that include one or more substances (e.g., heparin or heparan sulfate) which binds to an agent. For making hybrid matrices containing keratinocytes, the keratinocytes can be added to the mixture prior to the contraction step, or they can be added to the body of the composition after the gel has contracted.

In making any of the hybrid matrices of the invention, the gel can be formed in a flat-bottomed mold filled with the mixture to a depth of about 0.18 cm (e.g., about 0.1 cm to about 0.3 cm, preferably about 0.15 cm to about 0.21 cm). For example, the gel can be formed in a flat-bottomed cylindrical mold having an internal radius (r) using a mixture having a volume (V), such that $r^2/V$ is about 1.8 (e.g., 1.5 to 2.0). The invention includes hybrid matrices resulting from use of the specified depth of mixture, and/or the specified ratio of $r^2/V$, and thus having a characteristic thickness. The gel can be formed, for example, in a cylindrical mold having a radius of about 2.65 cm, using a volume of 4 ml, or in a mold the radius of which is other than 2.65 cm (i.e., larger or smaller), with a proportional change in volume of mixture used.

A medically useful polypeptide, such as one listed above, may be delivered to a patient by a treatment method that involves providing a hybrid matrix containing cells which secrete the polypeptide of interest, and implanting the article in the patient in a selected site, such as a subcutaneous, intraperitoneal, intraomental, sub-renal capsular, inguinal, intramuscular or intrathecal site. Where the polypeptide is one which promotes wound healing (e.g., PDGF or IGF-I), the matrix may be implanted at the site of a preexisting wound. As discussed above, the cells may be derived from one or more cells removed from the patient, and are preferably transfected in vitro with exogenous DNA encoding the polypeptide. Alternatively, they may be cells which naturally secrete the polypeptide or perform the desired metabolic function (e.g., hepatocytes or pancreatic beta cells). The cells can be induced to secrete the polypeptide, secrete higher amounts of the polypeptide, or perform the desired metabolic function by gene activation. Appropriate hybrid matrices for delivering a polypeptide to a patient can be any of those described above.

In another embodiment, the medically useful polypeptide may be administered to the patient by shunting a portion of the patient's blood through the apparatus described above, so that the polypeptide secreted by the cells in the hybrid matrix mixes with the blood. Generally, any such apparatus known to those in that field can be adapted to accommodate the matrix of the invention. For example, blood shunted into a device which contains a perm-selective membrane surrounding a matrix of the present invention will result in the delivery of a therapeutic product of the matrix to the blood. A device similar to an artificial pancreas (Sullivan et al., Science 252:718–721, 1991) may be used for this purpose. Again, any of the hybrid matrices described herein can be used for such devices.

Yet another use for any of the hybrid matrices of the invention is as a means for producing a polypeptide in vitro. This method includes the steps of placing the hybrid matrix under conditions whereby the cells in the matrix express and secrete the polypeptide; contacting the matrix with a liquid such that the cells secrete the polypeptide into the liquid; and obtaining the polypeptide from the liquid, e.g., by standard purification techniques appropriate for the given polypeptide. In one embodiment, the matrix is anchored to a surface and is bathed by the liquid; alternatively, the matrix floats freely in the liquid. Cells embedded in the hybrid matrix function at a high level in a small space. Furthermore, the first step in purification of the expressed polypeptide (removal of the cells from the medium) is considerably more efficient with the matrices than with most standard methods of cell culture.

As used herein, a "solid substrate" is an object, or a plurality of objects (configured, for example, as particles or threads), which acts as a reservoir or depot for a substance (e.g., a factor that promotes vascularization) that is contained within or is bound to the solid substrate. The substance is gradually released from the solid substrate into its environment. Where the solid substrate is in the form of beads, the beads have, generally, an approximately spherical shape and have a diameter of approximately 0.005–2.0 mm. Where the solid substrate is in the form of threads, the threads are generally about 0.01–1.0 mm in diameter. The threads can be folded into a meshwork or cut into small pieces (of approximately 5–10 mm) prior to gel formation. Where the threads are folded, their length should be, for example, about 1× to 3× (e.g., about 2×) the diameter of a mold used to produce the relevant hybrid matrix.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although other methods and materials similar or equivalent to those described herein can be used in the practice or testing of the present invention. All publications, patent applications, patents and other references mentioned herein are incorporated by reference in their entirety. The materials, methods, and examples described herein are illustrative only and not intended to be limiting.

Other features and advantages of the invention are apparent from the claims, and from the detailed description provided below.

DETAILED DESCRIPTION

Figure 1:
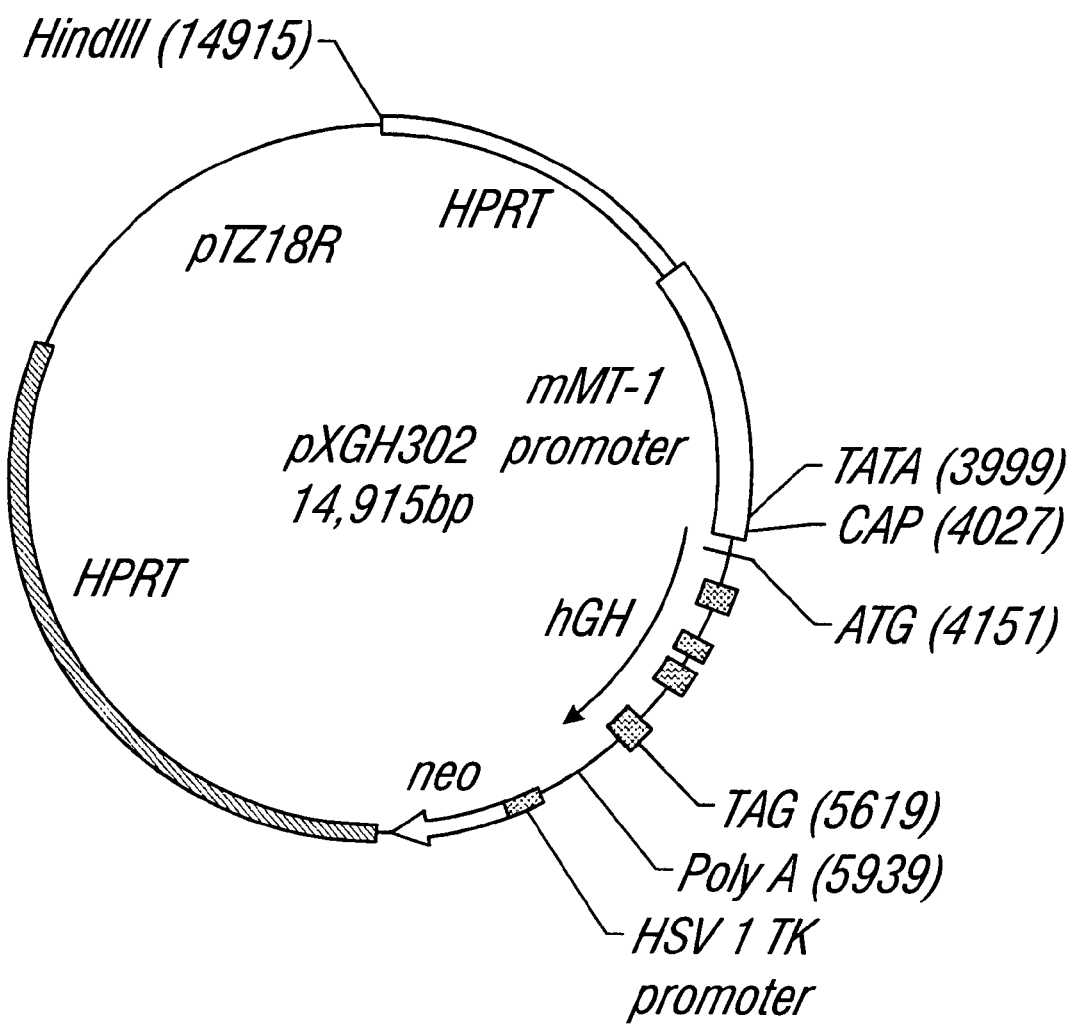
FIG. 1 is a map of hGH expression plasmid pXGH302.

The examples set forth below illustrate several embodiments of the invention. These examples are for illustrative purposes only, and are not meant to be limiting.

EXAMPLE I

This example describes the procedures utilized to prepare a clonal cell strain of human fibroblasts stably transfected with the plasmid pXGH302 secreting recombinant human growth hormone (hGH), and to combine them with porous collagen microspheres in a hybrid matrix of the invention. Such matrices are referred to as hybrid collagen matrices (HCM).

A. Generation of Primary Human Fibroblasts Expressing Human Growth Hormone

Fibroblasts were isolated from freshly excised human foreskins by an enzymatic dissociation technique. Upon confluency, primary cultures were dislodged from the plastic surface by mild trypsinization, diluted and replated to produce the secondary cell culture for transfection.

Plasmid pXGH302 was constructed as described in Example II, and transfection was carried out by electroporation, a process in which cells are suspended in a solution of plasmid DNA, placed between a pair of oppositely charged electrodes, and subjected to a brief electric pulse.

Treated cells were selected in G418-containing medium for 10–14 days. Cells that integrated the plasmid into their genomes stably expressed the product of the neo gene and formed colonies resistant to killing by the neomycin analog G418. Each colony, consisting of a clonal population of cells, was individually removed from its position on the tissue culture dish by trypsinization. Those clones scoring positive for hGH expression were expanded for quantitative assays, and clone HF165-24 was chosen for further use.

Further detailed procedures for preparing and transfecting cells suitable for use in the matrices of this invention are provided in WO93/09222 (PCT/US92/09627), which is incorporated herein by reference.

B. Preparation of Hybrid Collagen Matrices
1. Microsphere Preparation

Collagen microspheres (Cellex Biosciences cat. #YB00-0015UW) were transferred from each original bottle provided by the manufacturer (~10 ml per bottle) into 50 ml conical tubes (1 tube per bottle). The microspheres were allowed to settle in the tube, and the storage buffer solution was aspirated off. Microsphere wash medium (DMEM with 1% calf serum and 1% penicillin/streptomycin) was added to the 50 ml mark on the graduated tube, the microspheres allowed to settle, and the medium aspirated off. This series of washing steps was repeated for a total of 4 washes. The microspheres were transferred to a 250 ml Erlenmeyer flask using a 25 ml plastic pipette, limiting the volume of microspheres to 100 ml per 250 ml flask. Microsphere wash medium was added to the 250 ml mark, and the flask was capped and placed in a tissue culture incubator at 37° C. for 2–3 hours. The flask was removed from the incubator, the microspheres allowed to settle, and the wash medium aspirated off. This series of incubation and washing steps was repeated for a total of 3 washes.

2. Hybrid Collagen Matrix Preparation

The cells and microspheres were mixed just prior to adding the collagen solution. Washed microspheres were added to 15 ml graduated conical tube(s) to the desired volume (volume=no. of matrices multiplied by 1 ml; see Table 1). Microspheres were allowed to settle for at least 10 minutes before measuring volume. Excess wash medium was removed by aspiration.

Cells to be embedded in the matrix were harvested by trypsinization and the cell number was determined. The required number of cells (cell no. per matrix multiplied by total no. of matrices to be produced) was centrifuged at 1500 rpm (500×g) for 7 min at room temperature. In an appropriately sized conical-bottom polypropylene tube, a mixture of equal volumes of modified 2×DMEM (2×DMEM with 9 g/L glucose, 4 mM L-glutamine, and 22.5 mM HEPES) and calf serum was prepared according to Table 1. (Note: for volumes greater than 250 ml, the total pooled volume should be divided into appropriately sized tubes.) The cell pellet was resuspended in the 2×DMEM-calf serum mixture. The collagen microspheres were mixed with the cell suspension by adding 1–2 ml of the cell suspension to the packed microspheres and then transferring the concentrated microspheres by 10 ml pipette into the remaining cell suspension, followed by gentle mixing with the pipette. The mixture was placed on ice and the appropriate volume of collagen solution was added (rat tail Type I collagen; UBI cat #08-115, diluted to concentration of 4.0 mg/ml in 0.02 M acetic acid), as indicated in Table 1. The contents of the tube were mixed carefully (avoiding creating bubbles or frothing) using a 10 ml glass pipette, until the matrix solution appeared homogenous.

To produce the matrix, an appropriate volume of the collagen/cell/microsphere/medium mix was added to a sterile petri dish with a pipette (10 or 25 ml capacity), according to the total volume per dish listed in Table 1. (The mix was agitated by pipetting occasionally during the filling of dishes to prevent settling of cells or microspheres.) The filled dishes were placed in a 37° C., 5% $CO_2$, 98% relative humidity tissue culture incubator and left undisturbed for approximately 24 h, during which time the contents gelled and the size of the gel decreased in all dimensions to form the hybrid matrices of the invention, which were approximately 50% of the diameter and 10% of the volume of the non-gelled mixture.

Figure 2:
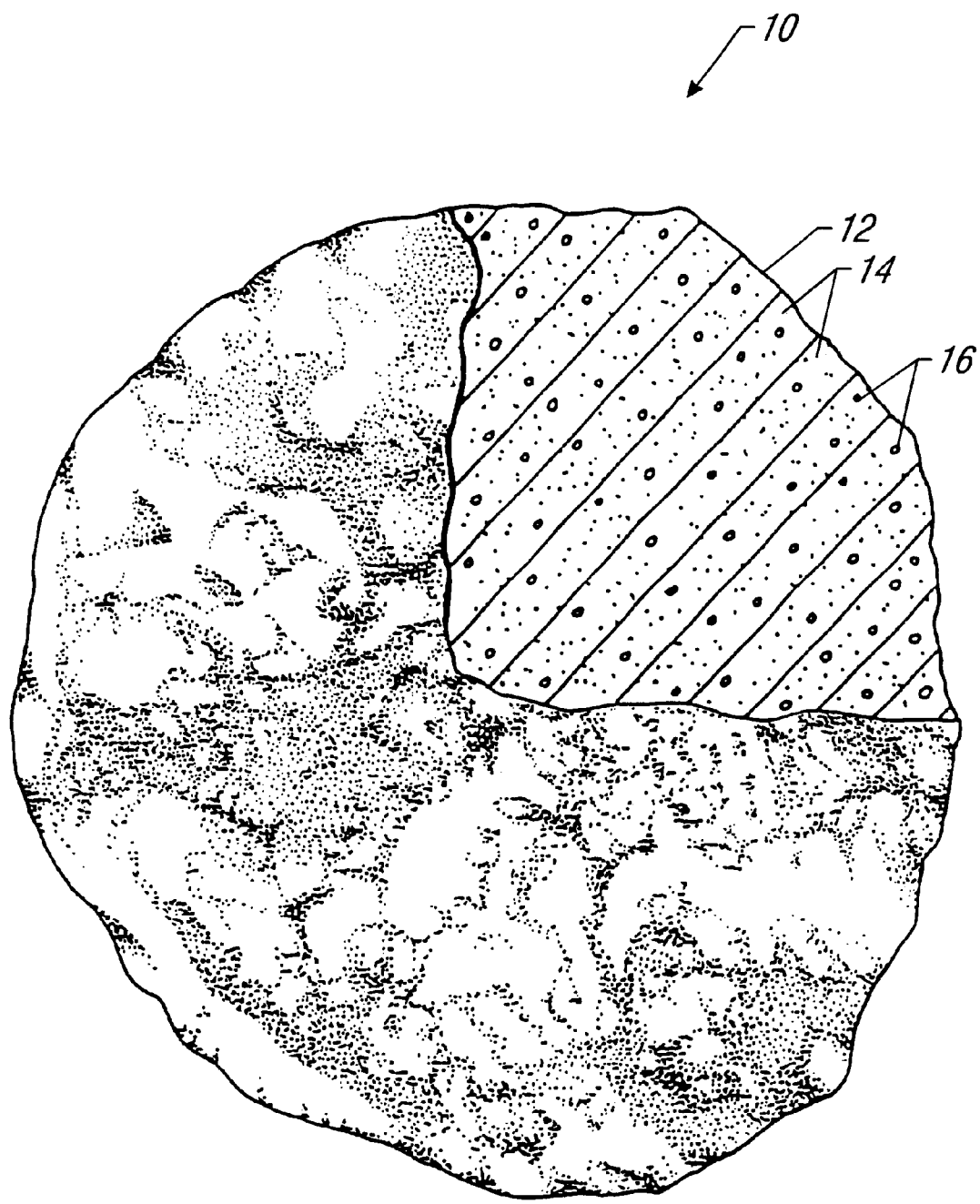
FIG. 2 is a plan view in partial section of one embodiment of the invention.

One embodiment of the hybrid matrix of the invention is illustrated in FIG. 2. The matrix 10 consists of a contracted collagen gel body 12 in which are embedded vertebrate cells 14 and microspheres 16. For clarity in this figure, the cells are shown as dots separate from the microspheres. In fact, most of the cells would be expected to be attached to the microspheres, and would be substantially smaller than represented in the figure.

TABLE 1

Medium, Microsphere, and Collagen Volumes Required for HCM Production

| Dish Size | Number of Matrices | Modified 2x DMEM | Serum | Microspheres | Collagen Solution | Total Vol. |
|---|---|---|---|---|---|---|
| 60 mm | 1 | 1 ml | 1 ml | 1 ml | 1 ml | 4 ml |
| 60 mm | 12 | 12 ml | 12 ml | 12 ml | 12 ml | 48 ml |
| 100 mm | 1 | 2.5 ml | 2.5 ml | 2.5 ml | 2.5 ml | 10 ml |
| 100 mm | 12 | 30 ml | 30 ml | 30 ml | 30 ml | 120 ml |
| 150 mm | 1 | 7.5 ml | 7.5 ml | 7.5 ml | 7.5 ml | 30 ml |
| 150 mm | 12 | 90 ml | 90 ml | 90 ml | 90 ml | 360 ml |

EXAMPLE II pXGH302 was constructed by subcloning the 6.9 kb HindIII fragment extending from positions 11, 960–18, 869 in the human HPRT sequence (Edwards et al., Genomics, 6:593–608, 1990; Genbank entry HUMHPRTB) and including exons 2 and 3 of the HPRT gene, into the HindIII site of pTZ18R (Pharmacia P-L Biochemicals, Inc.). The resulting clone was cleaved at the unique XhoI site in exon 3 of the HPRT gene fragment, and the 1.1 kb SalI-XhoI fragment containing the neo gene from pMClNeo (Stratagene) was inserted, disrupting the coding sequence of exon 3. One orientation, with the direction of neo transcription opposite that of HPRT, was chosen and designated pE3neo.

To combine the hGH gene, HPRT sequences, and neo gene in the same plasmid, pXGH5 (Selden et al., Mol. Cell. Biol. 6:3173–3179, 1986) was digested with EcoRI, and the 4.0 kb fragment containing the hGH gene and linked mouse metallothionein-I (mMT-I) promoter was isolated. The ExoRI overhangs were filled in with the Klenow fragment from E. coli DNA polymerase. pE3Neo was digested with XhoI, which cuts at the junction of the neo fragment and HPRT exon 3 (the 3' junction of the insertion into exon 3). The XhoI overhanging ends of the linearized plasmid were filled in with the Klenow fragment from *E. coli* DNA polymerase, and the resulting fragment was ligated to the 4.0 kb blunt-ended mMT/hGH fragment. Bacterial colonies derived from the ligation mixture were screened by restriction enzyme analysis for a single copy insertion of the mMT-I/hGH fragment. One subclone, in which the hGH gene is transcribed in the same direction as the neo gene, was designated pXGH302. A map of plasmid pXGH302 is shown in FIG. 1. In this figure, the position and orientation of the hGH coding region and the mouse metallothionein-I promoter (mMT-I) controlling hGH expression are noted. The positions of basal promoter elements (TATA), transcription initiation sites (CAP), and translation initiation sites (ATG) are indicated. As illustrated, neo gene transcription is controlled by the polyoma enhancer/herpes simplex virus (HSV) thymidine kinase (TK) gene promoter. HPRT denotes the positions of sequences from the human hypoxanthine-guanine phosphoribosyl transferase locus. Plasmid pXGH302 utilizes the pTZ18R (Pharmacia P-L Biochemicals, Inc.) backbone, a derivative of plasmid pUC18 (Yanisch-Perron et al., Gene 33: 103–119, 1985) carrying a T7 RNA polymerase promoter and the f1 origin of replication.

EXAMPLE III

This example illustrates a method of making a hybrid collagen matrix in which transfected cells prepared as described above are precultured with the microspheres prior to formation of the hybrid collagen matrix. Such "precultured" hybrid collagen matrices are referred to as PCHCM.

A. Preculture of Cells and Microspheres

Trypsinized transfected cells are seeded onto washed collagen microspheres at a ratio of $2 \times 10^6$ cells per ml microspheres (e.g. $10 \times 10^6$ cells onto 5 ml microspheres) by the following protocol:

1. Add cell suspension in a volume of growth medium that is twice the volume of the microspheres to a 125 ml Erlenmeyer flask. The limit is 10 ml of microspheres per flask.
2. Remove 1–2 ml of this suspension and add to 5 ml (packed volume) microspheres premeasured in a 15 ml tube.
3. Transfer cell suspension/microspheres back into the 125 ml Erlenmeyer flask.
4. Place flask into tissue culture incubator and swirl gently for approximately 5 seconds each hour for 4–5 h. Add growth medium to the 50 ml gradation on the flask, and allow cells and microspheres to incubate undisturbed overnight.

After 20–24h from the time of seeding, determine the number of cells attached to collagen microspheres by the following procedure:

1. Determine the weight of a 5 ml round bottom polystyrene test tube.

2. Remove a small sample of microspheres (0.1–0.2 ml) from the Erlenmeyer flask and add to the pre-weighed test tube.
3. Aspirate medium from microsphere sample and determine the weight of the tube plus sample. Calculate sample weight by subtracting weight of tube from weight of tube plus sample.
4. Add 1 ml of matrix digestion enzyme [collagenase IA (Sigma cat #C9891) at 1–2 mg/ml in PBS with $Ca^{2+}$ and $Mg^{2+}$] to microsphere sample and mix gently by tapping on the side of the tube.
5. Cover the tube with parafilm and place in a 37° C. water bath for 1 h, promoting disintegration of microspheres by pipetting through a Pasteur pipette at 15 minute intervals.
6. After 1 h incubation, further dissociate cells by pipetting vigorously with a 5 ml glass pipette. (Note: If clumps still remain, add to the tube a solution of 10× trypsin-EDTA at a volume ⅒th that of the volume of collagenase solution added, and incubate an additional 10 min.)
7. Perform cell counts using a hemacytometer.
8. Determine density of cells per ml microspheres using the following formula, which assumes that 50% of the wet packed volume of these microspheres is interstitial: Total number of cells/ml microspheres=1000 mg/(mg weight of sample)×(cell number in sample)×0.5.

The cell/microsphere mixture is transferred from the 125 ml Erlenmeyer flask to a 250 ml spinner flask (Bellco Microcarrier Spinner Flasks, 250 ml, with model #1965-60001 impeller shafts), growth medium is added to the 150 ml gradation mark, and the spinner flask is placed on a magnetic stirrer plate (set at 50 rpm) in a tissue culture incubator. The culture is fed with fresh medium the next day and 3 times weekly thereafter by allowing the microspheres to settle on the bottom of the flask, aspirating "spent" medium to the 50 ml mark on the flask, and adding fresh growth medium to the 200 ml mark. The density of cells per ml microspheres may be determined at desired time points as described above.

B. Preparation of Precultured Hybrid Collagen Matrices (PCHCM)

PCHCM are produced by the following protocol:

1. When the desired density of cells per ml microspheres is achieved (as determined by cell counts), remove microspheres containing cells from the spinner flask.
2. Produce matrices following the procedure outlined above for producing HCM, with the following modifications:
    i. Cells are not trypsinized.
    ii. Add cultured microspheres containing cells to 15 ml graduated conical tube(s), to the desired packed volume (volume=no. of matrices×0.5 ml).
    iii. Add empty microspheres to 15 ml graduated conical tube(s) to the desired packed volume (volume=no. of matrices×0.5 ml).
3. Prepare modified 2×DMEM and calf serum mixture as described in Example I above. Add both empty microspheres (50% of total microsphere volume) and microspheres containing cells (50% of total microsphere volume) to the modified 2×DMEM/calf serum mixture (see Table 2 below). The microsphere/DMEM/calf serum mixture is placed on ice and the appropriate volume of collagen solution is added (rat tail Type I collagen; UBI cat #08-115, diluted to concentration of 4.0 mg/ml in 0.02M acetic acid), as specified in Table 2. The contents of the tube are mixed carefully (avoiding creating bubbles or frothing) using a 10 ml glass pipette, until matrix solution appears homogenous.

TABLE 2

Medium, Microsphere, and Collagen Volumes Used for PCHCM Production

| Dish Size | Number of Matrices | Mod. 2x DMEM | Serum | Microspheres Empty | Microspheres Cultured | Collagen Solution | Total Vol. |
|---|---|---|---|---|---|---|---|
| 60 mm | 1 | 1 ml | 1 ml | 0.5 ml | 0.5 ml | 1 ml | 4 ml |
| 60 mm | 12 | 12 ml | 12 ml | 6 ml | 6 ml | 12 ml | 48 ml |
| 100 mm | 1 | 2.5 ml | 2.5 ml | 1.25 ml | 1.25 ml | 2.5 ml | 10 ml |
| 100 mm | 12 | 30 ml | 30 ml | 15 ml | 15 ml | 30 ml | 120 ml |
| 150 mm | 1 | 7.5 ml | 7.5 ml | 3.75 ml | 3.75 ml | 7.5 ml | 30 ml |
| 150 mm | 12 | 90 ml | 90 ml | 45 ml | 45 ml | 90 ml | 360 ml |

EXAMPLE IV

A. Hybrid matrices (HCM or PCHCM) are maintained in culture by feeding the matrices on day 1, and then 2 to 3 times weekly using the following protocol:

1. Carefully aspirate the culture medium.
2. Add the required volume of appropriate growth medium, taking into consideration the size of the dish used for each matrix (5–7 ml per 60 mm dish, 10–15 ml per 100 mm dish, 30–40 ml per 150 mm dish). The medium may be supplemented with ascorbic acid 2-phosphate and/or TGF-β (e.g. 10–50 Ag/ml ascorbic acid 2-phosphate and/or 1–10 ng/ml TGF-β).

B. The diameter of a hybrid collagen matrix can be determined using the following procedure:

1. Place the petri dish containing the matrix to be measured on top of a metric ruler resting on a dark background.
2. Record diameters (in centimeters) as desired: e.g., daily for the first 2 weeks, every other day after the first 2 weeks, and on days of cell quantitation for the duration of the experiment.

C. Cells can be recovered and quantified from a hybrid collagen matrix as follows:

1. Enzymatic Digestion of Hybrid Collagen Matrices
   a. Prepare a solution of collagenase IA (1.0 mg/ml for HCM and PCHCM, 2.0 mg/ml for HCM or PCHCM supplemented with ascorbic acid 2-phosphate and/or TGF-0) in PBS.
   b. Dispense the collagenase solution into 15 ml conical centrifuge tubes at a volume of 1 ml for matrices seeded with $1–5\times10^6$ cells and 5 ml for matrices seeded with greater than $5\times10^6$ cells per matrix. Prepare as many collagenase tubes as there are matrices to be counted.
   c. Remove each matrix from its dish using flat forceps, and carefully blot the excess fluid from the matrix using an absorbent paper towel (if cells will be discarded after counting) or sterile absorbent pad.
   d. Place each matrix in an individual collagenase-containing tube, cap tightly, and secure onto an orbital shaker set at 40 rpm in a tissue culture incubator.
   e. Incubate the matrices for approximately 1 hour or until digestion is complete. To accelerate digestion, break up the matrices by pipetting at 5 min intervals.
2. Cell Counting
   a. Measure the total volume of each digested cell suspension using the gradations on the side of the centrifuge tube.
   b. For measuring cell viability, remove 0.1 ml of cell suspension and add to 0.1 ml of 0.08% trypan blue in a 1.5 ml microcentrifuge tube. Mix by tapping the tube lightly.
   c. Count the viable and dead cells using a hemacytometer. If necessary, further dilute the cell suspension in PBS prior to adding the trypan blue. Calculate the total number of cells, taking into consideration the total volume measured in step 2a.

EXAMPLE V

This example describes experiments varying the inoculum density of clones of human fibroblasts stably transfected with the plasmid pXGH302 in a hybrid collagen matrix, to determine the cell density that can be supported in HCM. hGH production by each HCM was also monitored.

Hybrid collagen matrices were produced with 3 inoculum densities (ID) of the stably transfected hGH-expressing neonatal foreskin fibroblast clone designated HF165-24. The densities were 5, 10, and $20\times10^6$ cells per HCM. For each ID, 9 HCM were produced in 60 mm dishes. The hybrid matrix production medium for each ID consisted of 9 ml of modified 2×DMEM, 9 ml of calf serum, 9 ml of collagen microspheres, and 9 ml of 4 mg/ml soluble rat tail collagen, in 50 ml conical tubes.

HF165-24 harvested from monolayer cultures were pooled to provide enough of each ID for 9 HCM: $5\times10^6$ cells times 9 HCM=$45\times10^6$ cells total; $10\times10^6$ cells times 9 HCM=$90\times10^6$ cells total; $20\times10^6$ cells times 9 HCM=$180\times10^6$ cells total. Pooled cells for each ID were centrifuged at 1500 rpm for 7 min, supernatant was aspirated, and pellets were resuspended in 9 ml modified 2×DMEM and 9 ml calf serum and transferred to 50 ml tubes. Nine ml of collagen microspheres pre-measured in 15 ml graduated tubes were added to the cells/2×DMEM/calf serum mixture and mixed by gentle pipetting with a 10 ml pipette. This mixture was then placed on ice, and 9 ml of ice cold rat tail type I collagen solution (4 mg/ml) was added and mixed with a 10 ml pipette to produce a homogenous solution. Four ml of this mixture was added to each of nine 60 mm petri dishes for each density. The petri dishes were set in a tissue culture incubator and left undisturbed for 24 h. Medium was carefully aspirated from each dish after the 24 h incubation, and HCM were re-fed with Growth Medium (DMEM, 10% calf serum, and 1% Pen/Strep), using 5 ml per dish. To provide a greater volume of Growth Medium per matrix, HCMs were transferred on day 3 from 60 mm petri dishes to 100 mm petri dishes using flat forceps, and 10 ml of Growth Medium was added per dish. On day 6, medium was aspirated from each HCM, matrices were rinsed with 5 ml of Hank's Balanced Salt Solution (HBSS) and aspirated, and 10 ml of Growth Medium was added to each dish. The time of Growth Medium addition to HCM was noted in order to take a 24 h medium sample the following day (day 7). This rinse and feeding procedure was repeated on days 13 and 20 to provide day 14 and day 21 medium samples. The medium samples were assayed for hGH as indicated below. The HCM were also refed on days 10 and 17 without the rinse step.

Digestion of 3 HCM per ID for cell counts occurred on days 7, 14, and 21 after medium samples were taken, as described in Example IV. Production of hGH by HCM at the indicated time points was measured by radioimmunoassay (Nichols Institute) of the 24 h medium samples, as described in Example XII below. Table 3 summarizes the cell numbers for triplicate HCM of each ID, and hGH production by HCM at each ID on days 7 (n=9 matrices per condition), 14 (n=6 matrices per condition), and 21 (n=3 matrices per condition). Values are presented as mean +/− standard deviation. As indicated, the equilibrium density determined at days 14 and 21 for HCM prepared as described above is approximately $7\text{--}10 \times 10^6$ cells per matrix. Per cell hGH production for fully formed matrices at day 21 is similar among the 3 ID levels tested.

TABLE 3

Optimization of the Inoculum Density of HF165-24 Embedded in Hybrid Matrices for Cell Density and hGH Production.

| HCM ID | | µg hGH/ 24 h/matrix | µg hGH/24 h/ $10^6$ cells |
|---|---|---|---|
| | Cell # Day 7 | | |
| $5 \times 10^6$ | 5,331,000 ± 279,347 | 683 ± 138 | 130 ± 20 |
| $10 \times 10^6$ | 9,853,833 ± 858,634 | 716 ± 137 | 73 ± 6 |
| $20 \times 10^6$ | 13,226,000 ± 1,234,410 | 689 ± 130 | 50 ± 6 |
| | Cell # Day 14 | | |
| $5 \times 10^6$ | 6,534,000 ± 344,525 | 853 ± 232 | 133 ± 23 |
| $10 \times 10^6$ | 9,631,000 ± 875,820 | 1037 ± 277 | 108 ± 12 |
| $20 \times 10^6$ | 10,360,000 ± 706,541 | 840 ± 280 | 81 ± 16 |
| | Cell # Day 21 | | |
| $5 \times 10^6$ | 6,916,167 ± 608,352 | 730 ± 129 | 105 ± 10 |
| $10 \times 10^6$ | 9,884,833 ± 1,475,327 | 1004 ± 279 | 101 ± 20 |
| $20 \times 10^6$ | 10,207,750 ± 2,833,250 | 872 ± 333 | 83 ± 10 |

EXAMPLE VI

"Standard" collagen matrices (CM) do not include collagen microspheres. In order to compare CM with HCM, CM were prepared by replacing the volume occupied by microspheres in HCM with additional soluble collagen, to give a ratio of 1 part 2×DMEM, 1 part calf serum, and 2 parts soluble collagen per CM. A direct comparison of CM with HCM was assessed as follows.

The clone of human fibroblasts stably transfected with the plasmid pXGH302, designated HF165-24, was used. Nine matrices of each type, at each of two ID ($1 \times 10^6$ and $5 \times 10^6$ cells per matrix), were produced. For both CM and HCM, $9 \times 10^6$ cells (for $1 \times 10^6$ ID) and $45 \times 10^6$ cells (for $5 \times 10^6$ ID) were resuspended in 9 ml of 2×DMEM+9 ml of calf serum in 50 ml tubes. For CM, a total of 18 ml of rat tail type I collagen solution (4 mg/ml) was added to each ID set, and matrices were formed as described above in Example I. For HCM, 9 ml collagen microspheres and 9 ml of rat tail type I collagen solution (4 mg/ml) were added to each ID set, and HCM were formed according to Example I. Matrices were kept in the original 60 mm dish and fed with a volume of 5 ml Growth Medium. Cell numbers per matrix, as well as hGH production per matrix, were determined on days 7, 14, and 30 as described for Example V. The maximum cell densities (measured on day 14) and hGH production achieved by the 2 types of matrices at the 2 densities are summarized in Table 4. As indicated in the table, the hybrid type of matrix allowed for a higher density of cells and a substantially greater production of hGH per matrix, compared with the standard collagen matrix without microspheres.

TABLE 4

Comparison of "Standard" Collagen Matrices (CM) and Hybrid Collagen Matrices (HCM) for Maximum Cell Density and hGH Production by Embedded HF165-24 Cells

| Matrix Type | ID | Maximum cell Density | Maximum hGH Production Per matrix |
|---|---|---|---|
| CM | $1 \times 10^6$ | $2.1 \times 10^6$ | 290 µg |
| CM | $5 \times 10^6$ | $3.3 \times 10^6$ | 299 µg |
| HCM | $1 \times 10^6$ | $6.2 \times 10^6$ | 983 µg |
| HCM | $5 \times 10^6$ | $10.3 \times 10^6$ | 1221 µg |

EXAMPLE VII

This example describes the production and analysis of precultured hybrid collagen matrices (PCHCM). Cells of the clone of human fibroblasts stably transfected with the plasmid pXGH302 (HF165-24) were seeded onto collagen microspheres at a ratio of $2 \times 10^6$ cells per ml of microspheres, in the following manner: A suspension of $48 \times 10^6$ cells in 40 ml Growth Medium was obtained from harvested monolayer cultures. 5 ml of this suspension was added to each of four 15 ml graduated tubes containing 6 ml of packed collagen microspheres, and each cell/microsphere mixture was transferred to a 125 ml Erlenmeyer flask. An additional 5 ml of cell suspension was added to the cell/microsphere mixture in the 125 ml Erlenmeyer flask to give a final suspension of $12 \times 10^6$ cells with 6 ml microspheres and 10 ml Growth Medium per flask (4 flasks total). The flasks were placed in a tissue culture incubator and swirled gently for approximately 5 seconds each hour for 4 h. After the fourth hour, Growth Medium was added to each flask to the 50 ml mark, and flasks were left undisturbed for 24 h. At 24 h, the microspheres were transferred from each Erlenmeyer flask into a 250 ml spinner flask, Growth Medium was added to the 150 ml mark of each spinner flask, and flasks were placed on a magnetic stirrer plate set at 50 rpm in a tissue culture incubator. The following day, Growth Medium was added up to the 200 ml mark of each spinner flask, and flasks were refed 3 times weekly by aspirating medium to the 50 ml mark and adding fresh medium up to 200 ml.

On day 15 of the spinner flask culture, the density of cells per ml microspheres was determined. A small sample of microspheres (~0.1–0.2 ml) was removed from each flask and placed in pre-weighed 5 ml polystyrene tubes. Excess medium was removed from each tube by aspiration, and the tube containing the microsphere sample was weighed. One ml of a 2 mg/ml collagenase type IA solution in PBS was added to each tube, and the tubes were covered with parafilm, and placed in a 37° C. waterbath. At 15 minute intervals, the tubes containing microspheres were tapped lightly to disperse clumps. After 1 h, cells were further dissociated by vigorous pipetting with a 5 ml glass pipette. To further dissociate clumps, a solution of 10× trypsin:EDTA was added to give a final trypsin concentration of 1× in the collagenase solution, and the tubes were incubated for an additional 10 minutes. The dissociated cell suspensions were diluted 1:2 with PBS and added to hemacytometer chambers for cell counting. The density of cells per ml microspheres was calculated using the following formula:

Total # of cells/ml microspheres=1000 mg/(mg weight of sample)×(cell# in sample)×0.5.

This formula assumes that 1) wet collagen has a specific gravity of 1.0, and therefore the gram weight of collagen in the microsphere sample equals the collagen volume in milliliters, and 2) half of the wet packed volume of microspheres is occupied by interstitial volume. The average number of cells per ml microspheres (n=4 cultures per condition) for this experiment was $19.2 \times 10^6$. Microspheres were removed from each flask and pooled in a 15 ml graduated tube. The entire volume of 6 ml microspheres containing $19.2 \times 10^6$ cells per ml microspheres was used to produce hybrid collagen matrices.

In a 100 ml sterile bottle, 12 ml of modified 2×DMEM, 12 ml of calf serum, 6 ml of empty collagen microspheres, and the 6 ml of precultured microspheres were carefully mixed using a 10 ml glass pipette. This mixture was placed on ice, and 12 ml of ice-cold rat tail Type I collagen was added and mixed carefully using a 10 ml glass pipette. 4 ml of this mixture was added to each of twelve 60 mm petri dishes, and the dishes were placed at 37° C. and left undisturbed for 24 h.

The final number of cells per matrix was $9.6 \times 10^6$, since each matrix was composed of 0.5 ml of microspheres containing $19.2 \times 10^6$ cells per ml. These precultured hybrid collagen matrices (PCHCM) were refed after 24 h by aspirating the medium and adding 5 ml of Growth Medium. The PCHCM were refed on days 4, 7, 11, 14, 18, and 20 with 6 ml of Growth Medium. On days 7, 14, and 20, the PCHCM were also rinsed with 4 ml of HBSS prior to addition of medium, and the time of medium addition was noted. On days 8, 15, and 21, a 24 h medium sample was taken for assay of hGH production, and PCHCM were digested to obtain cell counts as follows: A solution of 2 mg/ml collagenase type IA in PBS was added at a volume of 6 ml per 15 ml tube. PCHCM were lifted from dishes with flat forceps and blotted on an absorbent paper towel prior to transfer into a collagenase solution. Tubes containing PCHCM and collagenase solution were secured onto an orbital shaker in a tissue culture incubator, the speed was set to 40 rpm, and PCHCM were allowed to digest for 2 h. After the 2 h incubation, PCHCM were dissociated into single cells by vigorous pipetting with a 5 ml glass pipette. Further dissociation was deemed necessary due to the presence of clumps, and a solution of 10× trypsin:EDTA (0.5% trypsin, 5.3 mM EDTA) was added to give a final trypsin concentration of 1× in the collagenase. The tubes were then incubated for an additional 10 min. Volumes in each tube were noted, and cell suspensions were diluted 2-fold in PBS and placed in a hemacytometer chamber to obtain cell counts. Production of hGH by PCHCM at the indicated time points was measured by radioimmunoassay of the 24 h medium samples, as described in Example VIII. Table 5 summarizes the cell numbers for triplicate PCHCM at each time point, and hGH production by PCHCM on days 8 (n=12 matrices per condition), 15 (n=9 matrices per condition), and 21 (n=6 matrices per condition). Values are presented as mean +standard deviation. As Table 5 shows, these PCHCM support a higher density of cells than the HCM described in Examples V and VI (Tables 3 and 4). The rate of hGH production per matrix and per cell was similar throughout the study period.

TABLE 5

HF165-24 Precultured on Collagen Microspheres and Embedded in Collagen to Form PCHCM: Cell Number and hGH Production Over Time in Culture.

| Day | Cell Number | μg hGH/24 h/matrix | μg hGH/24 h/$10^6$ cells |
|-----|-------------|---------------------|--------------------------|
| 8 | 13,732,000 ± 1,786,565 | 1264 ± 155 | 94 ± 10 |
| 15 | 12,573,000 ± 1,547,133 | 1317 ± 166 | 97 ± 14 |
| 21 | 13,706,000 ± 497,073 | 1254 ± 135 | 85 ± 10 |

EXAMPLE VIII hGH expression was monitored by quantitative hGH measurement with a sandwich radioimmunometric assay (Allegro hGH Assay, Nichols Institute, Cat. No. 40-2205), using conditions recommended by the manufacturer.

In order to determine the rate of hGH production, culture medium was changed 24 hours prior to harvesting the cells for passaging. At the time of passage an aliquot of the culture medium was removed for hGH assay, and the cells were then harvested, counted, and reseeded. hGH levels are calculated after counting the harvested cells, and are expressed as Ag hGH/24 hr/$10^6$ cells.

EXAMPLE IX

This example describes in vivo implantation of hybrid collagen matrices (HCM) prepared as described in Example I, as well as standard collagen matrices (CM) prepared as described in Example VI.

For subcutaneous implantation of matrices, mice [M. musculus strains N:NIH(S)-nu/nu (nude; Taconic Farms, Germantown, N.Y.) were given an intraperitoneal injection of avertin (solution of 2% w/v 2,2,2-tribromoethanol and 2% v/v 2-methyl, 2-butanol) at a dose of 0.0175 ml/g body weight. Anesthetized mice were placed in lateral recumbency, and the skin prepped with alcohol and Betadine. A 0.5 cm to 1 cm transverse incision was made on the animal's left flank. The subcutaneous space was enlarged by sharp dissection to an area slightly larger than the size of the matrix to be implanted. The matrix was placed horizontally in the subcutaneous space and spread evenly with the use of Millipore forceps. The incision was closed, using stainless steel surgical staples.

Blood was collected by retroorbital bleed after placing the mouse in a large beaker containing methoxyflurane (Pittman-Moore) until light anesthesia was achieved. Serum hGH levels were determined using the commercially available sandwich radioimmunometric assay described above. The assay was performed as described as recommended, except that control serum from untreated mice was used to obtain corrected cpm for generating the standard curve.

CM and HCM were prepared for implantation into nude mice as described in Examples I and VI, using hGH-expressing HF165-24 cells. In the first experiment (Experiment 1, Tables 6 and 7), 13 matrices of each type were prepared. HCM were produced with an inoculum density (ID) of $5\times10^6$ HF165-24 cells per matrix, and standard collagen matrices (CM) were produced with an ID of $2\times10^6$ HF165-24 per matrix. Fewer cells were used to inoculate the CM since these matrices do not support as high a cell density as HCM (see Examples V and VI). In subsequent experiments (Experiments 2 and 3, Tables 6 and 7) only HCM matrices were tested (13 in each of Experiments 2 and 3). Matrices were kept in the original 60 mm dishes and fed with 5 ml of growth medium. After 13 days in culture, all of the dishes were fed with fresh growth medium; 24 h later triplicate matrices of each set were digested for cell counts, and medium samples from all 13 matrices in each set were assayed for hGH.

For Experiment 1, at the time of implantation the average number of cells in the CM was $2.4\times10^6$ cells/matrix, while the average number of cells in the HCM was $7.4\times10^6$ cells/matrix (Table 6). The cell number per matrix was similar to the latter for the HCM prepared in Experiments 2 and 3 ($8.9\times10^6$ and $9.2\times10^6$ cells per HCM matrix, respectively). Table 6 summarizes the cell number (n=3 matrices per condition), in vitro hGH production per matrix (n=13 matrices per condition), and specific production rate (ug/$10^6$cells/24 h; n=3 matrices per condition) for each set of in vitro experiments. Values are presented as mean±standard deviation. As shown in Table 6, HCM supported a higher density of cells and produced a higher level of hGH on the day of implantation than did the CM.

TABLE 6

HF165-24 Cell Density and In Vitro hGH Production per Matrix for Collagen Matrices and Hybrid Collagen Matrices on Day of Implantation

| Experiment # | Cell # on Day of Implantation | μg hGH/24 h/matrix | μg hGH/24 h $10^6$ cells |
|---|---|---|---|
| 1/CM | $2.4 \pm 0.1 \times 10^6$ | 241 ± 33 | 98 ± 8 |
| 1/HCM | $7.4 \pm 1.6 \times 10^6$ | 983 ± 239 | 109 ± 16 |
| 2/HCM | $8.9 \pm 1.5 \times 10^6$ | 1399 ± 177 | 170 ± 27 |
| 3/HCM | $9.2 \pm 0.9 \times 10^6$ | 1279 ± 115 | 137 ± 19 |

Figure 3:
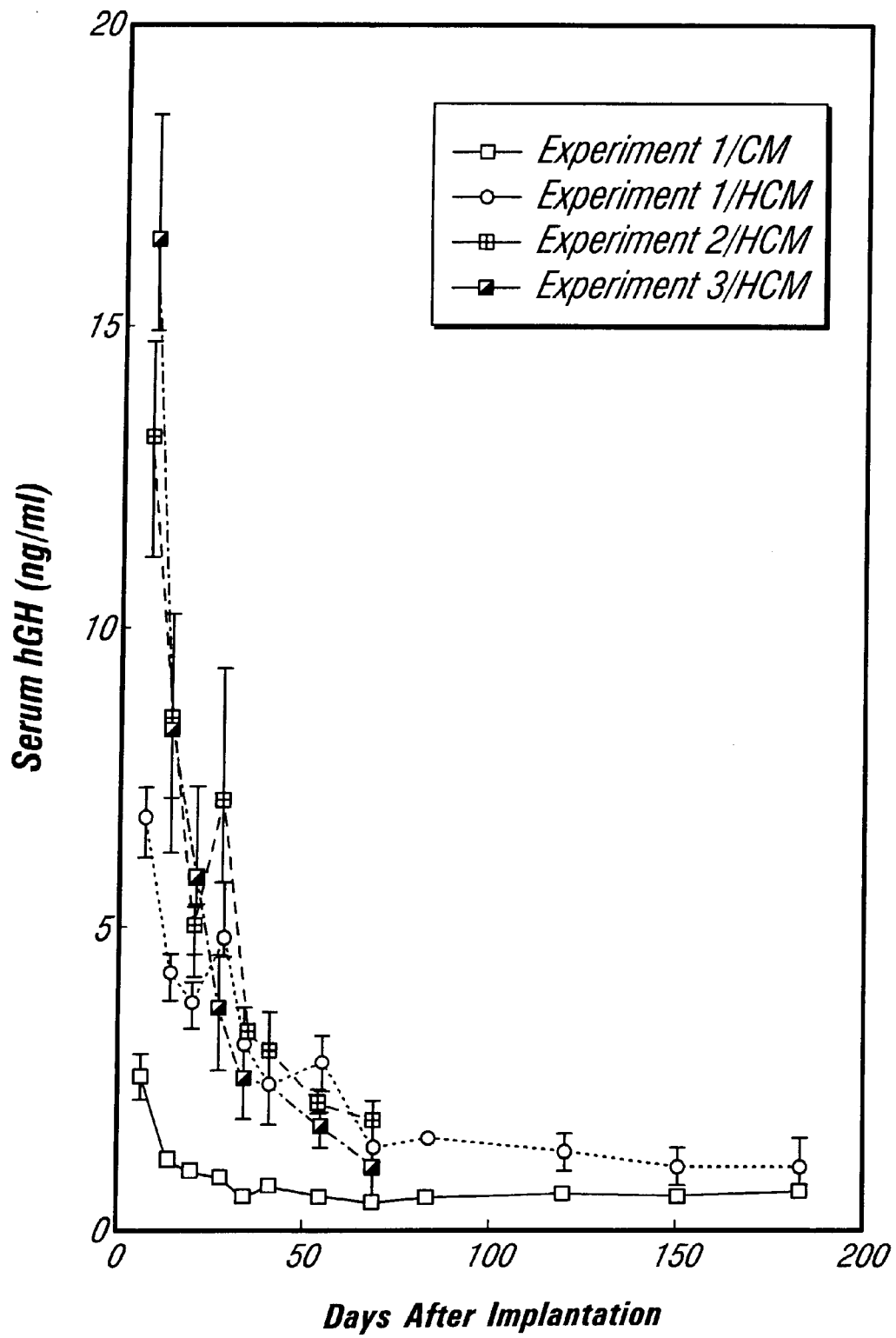
FIG. 3 is a graph showing the in vivo hGH levels in nude mice implanted with either a collagen matrix or a hybrid collagen matrix containing HF165-24 cells, human skin fibroblasts stably transfected with pXGH302 and expressing hGH.

Eight matrices of each type were implanted into nude mice in Experiment 1, while five HCM were implanted into nude mice in each of Experiments 2 and 3. Serum hGH levels were measured at regular intervals after implantation. The results are shown in Table 7 and FIG. 3. In Experiment 1, HCM-implanted animals maintained substantially higher serum hGH levels than did CM-implanted animals for 186 days post-implantation. Animals implanted with HCM in Experiments 2 and 3 showed similarly high serum hGH levels.

TABLE 7

In Vivo Delivery of hGH by Implanted Collagen Hybrid Matrices Containing Transfected Human Skin Fibroblasts

| | serum hGH values (ng/ml ± standard error) | | | |
|---|---|---|---|---|
| | Experiment 1 | | Experiment 2 | Experiment 3 |
| Days After Implantation | CM n = 8 | HCM n = 8 | HCM n = 5 | HCM n = 5 |
| 7 | 2.4 ± 0.4 | 6.8 ± 0.6 | 13.2 ± 2.0 | 16.5 ± 2.1 |
| 14 | | | 8.5 ± 1.3 | 8.3 ± 2.0 |
| 15 | 1.0 ± 0.1 | 4.2 ± 0.4 | | |
| 21 | 0.8 ± 0.1 | 3.7 ± 0.4 | 5.0 ± 0.4 | 5.8 ± 1.6 |

TABLE 7-continued

In Vivo Delivery of hGH by Implanted Collagen Hybrid Matrices Containing Transfected Human Skin Fibroblasts

| | serum hGH values (ng/ml ± standard error) | | | |
|---|---|---|---|---|
| | Experiment 1 | | Experiment 2 | Experiment 3 |
| Days After Implantation | CM n = 8 | HCM n = 8 | HCM n = 5 | HCM n = 5 |
| 28 | | | 7.1 ± 2.3 | 3.6 ± 1.0 |
| 29 | 0.7 ± 0.1 | 4.8 ± 1.0 | | |
| 35 | 0.4 ± 0.1 | 3.0 ± 0.7 | 3.2 ± 0.3 | 2.4 ± 0.6 |
| 42 | 0.6 ± 0.1 | 2.3 ± 0.3 | 2.9 ± 0.7 | 2.3 ± 0.6 |
| 55 | | | 2.0 ± 0.3 | |
| 56 | 0.4 ± 0.1 | 2.7 ± 0.5 | | 1.6 ± 0.3 |
| 70 | 0.3 ± 0.0 | 1.2 ± 0.2 | 1.7 ± 0.4 | 0.9 ± 0.4 |
| 85 | 0.4 ± 0.1 | 1.4 ± 0.2 | | |
| 123 | 0.5 ± 0.1 | 1.2 ± 0.3 | | |
| 154 | 0.5 ± 0.1 | 1.0 ± 0.3 | | |
| 186 | 0.6 ± 0.1 | 1.0 ± 0.5 | | |

EXAMPLE X

The hybrid matrices of the invention would be prepared for implantation in humans as follows:

The desired cells, typically stably transfected autologous cells derived from the patient, are harvested from tissue culture dishes and processed for the production of HCM or PCHCM by any of the methods described in Examples I–IV. The dosage for a given patient (i.e. the physiologically effective quantity of therapeutic product produced by the matrix) can be varied by using a larger or smaller matrix, implanting a different number of matrices into the patient, and/or using cells which express a different level of the product per cell when constructing the matrix. The quantity of the therapeutic product produced in the patient may also be varied by exposing the cells in the matrix to a pharmacologic or physiologic signal which alters expression of the therapeutic gene. For example, if the therapeutic gene is under the control of a glucocorticoid-responsive promoter, then in vivo exposure of the cells to a drug such as dexamethasone (by administering the drug to the patient in a manner that ensures the drug reaches the implant) will alter expression of the therapeutic gene.

Typically, a plurality of small matrices (approximately 1–2 cm) in diameter, produced in 60 mm petri dishes and containing on the order of $10\times10^6$ cells per matrix, would be implanted. Thus, approximately 100 million cells could be implanted using 10 small matrices. The use of matrices with significantly higher cell densities (as produced by incorporating, for example, ascorbic acid 2-phosphate) would result in a smaller number of matrices needed for a given patient. Alternatively, a larger petri dish (>150 mm diameter) may be used as a mold to produce larger matrices which could be either implanted directly or cut into smaller pieces which are implanted.

Prior to implantation, the matrices may be stored or shipped in growth medium or any other solution which allows the cells to remain viable. Alternatively, the matrices may be cryopreserved by freezing in an appropriate freezing medium, which can be washed away prior to implantation.

Matrices may be implanted in a variety of sites, including, but not limited to, subcutaneous, intraperitoneal, intrasplenic, intraomental, inguinal, intrathecal, intraventricular, and intramuscular sites, as well as within lymph nodes or within adipose tissue. A surgical incision at the appropriate site is made, the matrix inserted, and the incision closed.

EXAMPLE XI

There are a number of static and perfusion large scale in vitro culture systems that can be adapted for use in protein manufacture using cells maintained in hybrid matrices of the invention. The choices offer varying levels of facility in the necessary steps of feeding and medium harvest prior to purification of target proteins. Several are described below.

1. After formation and maturation of hybrid collagen matrices (HCM) in conventional petri plates (e.g. after 10–25 days incubation), a number of these HCM can be aseptically transferred to a sterile Microsphere Spinner Flask (250–100 ml capacity). These HCM are produced and maintained under conditions which maximize the viable cell density within each matrix. Typically this requires between 5 and 20 ml medium for every one ml of matrix volume. The protein production medium is formulated to comprise a minimum of undefined components (e.g., serum), and may include added factors intended to maximize the output of protein production per cell. The spinner flasks are placed into a 37°±1° C., 5%±1% $CO_2$ humidified incubator on a magnetic stir platform set for 30–70 rpm. After 1–3 days, the flask is transferred to a class 100 biological safety cabinet, and the production medium containing the expressed protein is aseptically drawn off without disturbing the settled matrices. An equivalent volume of fresh protein production medium is added to the flask, and the flask is returned to the stir platform within the incubator.

2. The matrices described in (1) above may be aseptically transferred into a 1–5L bioreactor (e.g, Brunswick) with a controllable stirring impeller shaft. Production medium level is set by the control system of the bioreactor. Medium harvesting and replenishment is controlled within a sterile closed loop system to minimize contamination.

3. For high volume HCM production, the matrices are formed from the constituent components and allowed to gel within a tissue culture roller bottle. The bottles are incubated in a static upright position until contraction of the matrix results in a free-floating structure (3–5 days). Growth medium is then replenished, and the bottles are gassed with 5% $CO_2$ and placed into a roller apparatus within a 37° C. incubator. Growth medium is replenished every 2–3 days until HCM are mature (10–25 days total incubation), at which time the HCM are exposed to protein production medium. After 1–3 days, the bottles are transferred to a class 100 biological safety cabinet and the production medium containing the expressed protein is aseptically drawn off without disturbing the matrices. An equivalent volume of fresh protein production medium is added to the bottle, which is returned to the roller apparatus.

4. The constituents of the HCM can be aseptically introduced into sterile gas-permeable Teflon™ bags through a sealable port. The components are allowed to gel within the bag and take on the shape and conformation therein. Bags are incubated in 37°±1° C., 5%±1% $CO_2$ humidified incubators. As the HCM contract and reduce in volume, the growth medium volume is adjusted to compensate. Medium harvesting and replenishment is accomplished through sterile-connect tube systems built into the bags. The use of ported incubators and extended tubing would allow for the design of a cyclic harvest/feed pumping system that could eliminate the need for removing the bags from incubators during a production run.

5. The constituents of the HCM can be aseptically introduced into custom-designed thermoformed trays with a high volume capacity. The simplest conformation would be an open lidded rectangular tray with gas exchange capabilities designed for use in a $CO_2$ tissue culture incubator. Another design would include a closed loop system with ported access to the medium reservoir for controlled feeding and medium harvest, akin to a bioreactor chamber.

EXAMPLE XII

General Description of Heparin-Sepharose Hybrid Collagen Matrices (HSHCM)

HSHCM are produced by mixing together concentrated DMEM, collagen (e.g., rat tail type I or a suitable alternative, for example, human placental type I and III collagen), microspheres (for example, collagen macroporous microspheres as described above or porous gelatin microspheres), heparin-Sepharose beads either uncoated or coated with an angiogenic factor, a cytokine, or a growth factor (for example, basic fibroblast growth factor (bFGF), vascular endothelial growth factor (VEGF), or platelet derived growth factor (PDGF)), and cells expressing the therapeutic protein. In an alternative embodiment, a combination of cell strains are mixed into the matrix, with one strain expressing the therapeutic protein of interest and the other strain expressing the angiogenic or growth factor. It is also possible to utilize a single strain that expresses both the therapeutic protein and the angiogenic or growth factor. In this embodiment, the heparin-Sepharose bead component may be uncoated or coated with the same or a different growth factor from the one expressed by the incorporated cell strain, or it may be omitted altogether.

Microsphere Preparation

The preparation of collagen microspheres for matrix production is as described above. The preparation of gelatin microspheres was performed as follows. One gram of dry Cultisphere-GL™ gelatin microspheres (Hyclone Catalog # DG-1001-00) was placed in a 100 ml glass bottle containing 50 ml of phosphate-buffered saline without calcium or magnesium (PBS). The gelatin microspheres were allowed to hydrate for at least an hour at room temp. They were sterilized by autoclaving at 121° C. for 15 min. The gelatin microspheres were conditioned for use in matrices by removing the PBS and washing 3× in DMEM+1% calf serum+1% Penicillin-Streptomycin (50 ml per wash). The gelatin microspheres were swirled gently and allowed to settle between washes. Conditioned Cultisphere-GLt™ gelatin microspheres can be stored at 4° C. prior to use.

Heparin-Sepharose Bead Preparation

Heparin coupled to Sepharose® agarose beads provides a solid support for the attachment of heparin-binding growth factors such as bFGF, VEGF, and PDGF. Sepharose® is a highly cross-linked agarose resin manufactured by Pharmacia Biotech and is a registered trademark of the manufacturer. Heparin linked to a different type of support matrix (for example, a polymer) can be used instead of a heparin-agarose bead. Heparin-Sepharose® 6 Fast Flow beads (Pharmacia Biotech Cat #17-0998-03) were washed 3× in $dH_2O$ at 5× the bead volume per wash. The beads were swirled gently after addition of $dH_2O$ and centrifuged at 500×g between each wash step. They were sterilized by autoclaving at 121° C. for 20 min. The beads were equilibrated at pH 7.2–7.4 by extensive washing in PBS until the pH of the 1:1 bead to PBS slurry was within the range of 7.2–7.4. The beads were stored at 4° C. in 1:1 slurry with PBS.

Angiogenic and growth factors were bound to the heparin-Sepharose® beads as follows. Equilibrated beads were placed in an appropriate size sterile tube (for example, a 1.5 ml Eppendorf or a 15 ml conical tube) and centrifuged at 500×g for 4 min. They were washed 2× in PBS, with a centrifugation step between each wash. The angiogenic or growth factor (e.g., at 50 µg/ml in the case of bFGF) was added to the beads in a volume of PBS equal to the packed bead volume to give a 1:1 bead to PBS slurry, and the binding was performed under rotation (for example, on a Nutator™ platform at room temp. for 1 h. The PBS containing any unbound growth factor was removed from the beads by aspiration, and the beads were washed 1× in PBS at a volume equal to the packed bead volume. The PBS was removed, and the beads were placed on ice until matrix formation.

HSHCM Preparation

The different components used to prepare HSHCM are listed in Tables 8 and 9. These tables describe production of HSHCM using collagen microspheres (Table 8) or gelatin microspheres (Table 9). Each table gives the volume of each component per ml of production medium, as well as the volume necessary for production of 10×4 ml HSHCM as an example. (Volumes and concentrations given for matrices hereinbelow refer to the pre-contraction volume and concentration, respectively.) The matrix "pre-mix" consists of 10× DMEM, 7.5% NaHCO$_3$, 1M HEPES, Penicillin-Streptomycin, L-glutamine, and dH$_2$O. The pre-mix was generally prepared an hour or two prior to mixing with collagen, cells and the angiogenic factor-coated beads, and kept at 4° C. Cells to be embedded in the HSHCM were harvested and prepared as described in Example 1. The cell pellet was resuspended in a volume of growth medium equal to 10% of the total volume of HSHCM production medium as indicated in Tables 8 and 9. The density of cells per ml matrix can vary as appropriate (e.g., 0.1–10×10$^6$ cells per ml matrix). Since the cell suspension was added at a volume that is 10% of the total production medium volume, the number of cells per ml of this suspension was 10× greater than the desired density of cells per ml matrix (e.g. 1–100×10$^6$ cells per ml). The appropriate volume of microspheres is placed in a conical tube, and the cell suspension was added to the microspheres. Using a 10 ml plastic pipette, the cells and microspheres were mixed together and set aside at room temp. for approximately 10 to 15 minutes prior to incorporation into the production medium. The pre-mix was placed on ice and a solution of collagen (e.g., rat tail collagen (RTC)) was added to the chilled pre-mix and mixed thoroughly using a 10 ml plastic pipette. The pH of the production medium was then adjusted to approximately 7.8 by addition of iN NaOH at the volume indicated in Table 8 or 9. The cell/microsphere mixture was added to the neutralized production medium and mixed using a 10 ml plastic pipette. A volume of growth medium equal to the packed volume of heparin-Sepharose beads was added to the beads, and the beads were transferred to the production medium and mixed using a 10 ml plastic pipette. A volume of this final HSHCM production medium was added to the appropriate size Petri dish. For example, 4 ml of HSHCM production medium is generally added to a 60 mm Petri dish, 10 ml to a 100 mm Petri dish, and 30 ml to a 150 mm Petri dish. Varying the ratio of production medium volume to dish surface area can modify the thickness of the HSHCM (see Example XVIII). The dishes containing the HSHCM production medium were transferred to an incubator with a temperature of 37° C., humidity of 95 to 98%, and a CO$_2$ level of 5%. One hour later, the dishes were removed from the incubator and examined. If the HSHCM production medium had gelled, the HSHCM were fed by addition of 5 ml of growth medium. Otherwise, the dishes were returned to the incubator for an additional hour or until polymerization was complete, at which time the HSHCM were fed by addition of 5 ml of growth medium. The growth medium was supplemented with 10–100 ng/ml of the same growth factor or angiogenic factor used to coat the heparin-Sepharose beads of the HSHCM.

TABLE 8

HSHCM Production Media Formulation: Collagen Microsphere Configuration.

| Component | Volume (per ml) | Total Vol. for 10 × 4 ml matrices | Final Conc. |
|---|---|---|---|
| 10 X DMEM | 0.1 ml | 4.0 ml | 1 X |
| 7.5% NaHCO$_3$ | 0.012 ml | 0.48 ml | 0.9 g/L |
| 1 M HEPES | 0.0025 ml | 0.1 ml | 2.5 mM |
| Pen/Strep (100 X stock) | 0.01 ml | 0.4 ml | 1% |
| L-glutamine (200 mM stock) | 0.01 ml | 0.4 ml | 2 mM |
| dH$_2$O | 0.16 ml | 6.4 ml | 16% |
| RTC (4 mg/ml, 0.02 N acetic acid) | 0.25 ml | 10 ml | 1 mg/ml |
| 1 N NaOH (to pH 7.4–7.8) | 0.005 ml | 0.2 ml | 0.5% |
| Collagen microspheres* | 0.25 ml | 10 ml | 25% |
| Cell suspension* | 0.1 ml | 4.0 ml | 10% |
| Heparin-Sepharose beads (as a 1:1 slurry in DMEM + 10% calf serum)* | 0.1 ml | 4.0 ml | 5.0% dry weight |
| Total Volume | 1.0 ml | 40.0 ml | |

*Added to the production medium after pH is adjusted

TABLE 9

HSHCM Production Media Formulation: Gelatin Microsphere Configuration.

| Component | Volume (per ml) | Total Vol. for 10 × 4 ml matrices | Final Conc. |
|---|---|---|---|
| 10 X DMEM | 0.1 ml | 4.0 ml | 1 X |
| 7.5% NaHCO$_3$ | 0.012 ml | 0.48 ml | 0.9 g/L |
| 1 M HEPES | 0.0025 ml | 0.1 ml | 2.5 mM |
| Pen/Strep (100 X stock) | 0.01 ml | 0.4 ml | 1% |
| L-glutamine (200 mM stock) | 0.01 ml | 0.4 ml | 2 mM |
| dH$_2$O | 0.15 ml | 6.0 ml | 15% |
| RTC (4 mg/ml, 0.02 N acetic acid) | 0.438 ml | 17.5 ml | 1.75 mg/ml |
| 1 N NaOH (to pH 7.4–7.8) | 0.015 ml | 0.6 ml | 1.5% |
| Gelatin microspheres* | 0.0625 ml | 2.5 ml | 6.25% |
| Cell suspension* | 0.1 ml | 4.0 ml | 10% |
| Heparin-Sepharose beads (as a 1:1 slurry in DMEM + 10% calf serum)* | 0.1 ml | 4.0 ml | 5.0% dry weight |
| Total Volume | 1.0 ml | 40.0 ml | |

*Added to the production medium after pH is adjusted

In Vitro Maintenance and Evaluation of HSHCM

HSHCM were maintained in culture as described above for HCM in example IV. The volume of growth medium used to feed the matrices is usually the maximum volume that can be added to each dish size, for example, 10 ml per 60 mm dish, 20–30 ml per 100 mm dish, and 100–150 ml per 150 mm dish. Matrix size and cell number per matrix were determined as described for the HCM.

EXAMPLE XIII

This example describes in vivo implantation of HSHCM prepared as described in Example XII. HSHCM containing either uncoated heparin-Sepharose beads or heparin-Sepharose beads coated with bFGF (50 µg/ml packed beads; 10 µg total bFGF/matrix) were prepared as described in Table 8. Each 4 ml matrix was formed with $5 \times 10^6$ cells of HF743 B1-35, a human foreskin fibroblast clone containing plasmid pXF8.198 and expressing hFVIII at levels between 20,000–30,000 mU/24h/$10^6$ cells. The HSHCM were maintained in culture for 2 days prior to implantation. For subcutaneous implantation of matrices, Rag-2 mice (129S6/SvEvTac-[KO]Rag2, Taconic Farms) were anesthetized and prepped as described in Example IX. The implant site was shaved and disinfected with alcohol and Betadine. A 2 cm incision was made in the cutaneous layer on the left side of the animal, inferior and caudal to the ribs, and the fascia between the cutaneous and external oblique muscle layer was cleared and enlarged using sterile blunt scissors. HSHCM were prepared for implantation by washing 2× in 10 ml of PBS. Each matrix was folded into quarters using sterile spoon-shaped spatulas, and inserted into the cleared cutaneous space using a sterile spatula. The incision was closed using wound clips.

Figure 4:
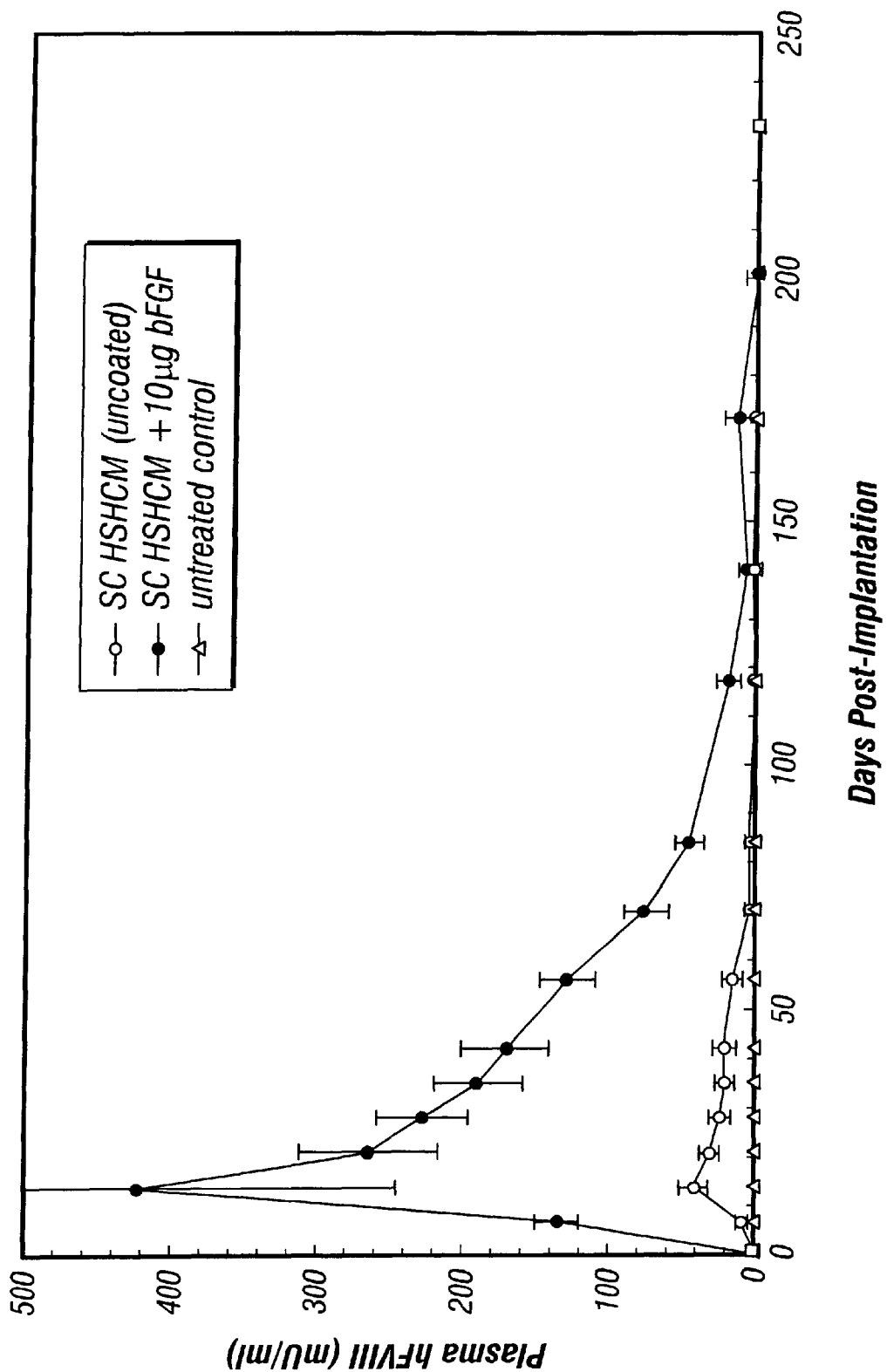
FIG. 4 is a line graph showing levels of human factor VIII (hFVIII) in plasma from mice implanted with Heparin-Sepharose Hybrid Collagen Matrices (HSHCM) containing cells producing hFVIII and heparin-Sepharose beads either coated with basic fibroblast growth factor (bFGF) or uncoated.

Blood was collected as described in Example IX. Plasma hFVIII was determined using a hFVIII ELISA based on two mouse monoclonal antibodies [Hornsey et al. (1992) Transfus. Med. 2(3):223–229]. The estimated number of cells per matrix was determined by digesting and counting recovered cells from HSHCM set aside for this purpose. HSHCM containing uncoated heparin-Sepharose beads had an average of $2.8 \times 10^6$ cells per matrix and HSHCM containing bFGF-coated heparin-Sepharose beads had an average of $3.1 \times 10^6$ cells per matrix (n=3 matrices per condition). The in vitro production of hFVIII from each matrix type on the day of implantation was 71,165 mU/24 h and 85,657 mU/24 h from HSHCM containing uncoated and bFGF-coated beads, is respectively (n=3 matrices per condition). As shown in FIG. 4, HSHCM containing bFGF-coated heparin-Sepharose beads led to a significantly higher plasma level of hFVIII detected in the host mice as compared to HSHCM without the growth factor (n=10 mice per condition). There was no detectable hFVIII on day 0, and the peak plasma level occurred on day 14.

The following examples describe additional studies involving subcutaneous implantation of HSHCM (prepared as described in Example XII) into Rag-2 mice, and utilize the HF743-B1-35 hFVIII secreting cell clone introduced above. Time of implantation and implant procedures are identical to that described in Example IX unless otherwise indicated.

EXAMPLE XIV

HSHCM containing either uncoated heparin-Sepharose beads or heparin-Sepharose beads coated with bFGF (50µg/ml packed beads, 10 µg total bFGF/matrix), and either collagen microspheres or gelatin microspheres, were prepared as described in Tables 8 and 9, respectively. The average number of cells per matrix and hFVIII production per matrix on the day of implantation (n=3 matrices per condition) are listed in Table 10.

TABLE 10

Summary of cell number and hFVIII production per HSHCM on the day of implantation.

| Condition | Cell # (× $10^6$) | hFVIII (mU/24 h/HSHCM) |
|---|---|---|
| Collagen microspheres & uncoated heparin-Sepharose beads | 4.2 | 84,989 |
| Gelatin microspheres & uncoated heparin-Sepharose beads | 3.9 | 94,407 |
| Collagen microspheres & bFGF-coated heparin-Sepharose beads | 4.3 | 138,612 |
| Gelatin microspheres & bFGF-coated heparin-Sepharose beads | 3.5 | 107,683 |

Subcutaneous (SC) cell controls were included in this experiment and were prepared as follows. Cells were harvested by trypsinization in the same manner as for preparation of HCM. The trypsinized cells were counted, centrifuged at 500×g, resuspended in Hank's Buffered Saline Solution (without calcium and magnesium), centrifuged, and resuspended in a volume of PBS to give $100 \times 10^6$ cells/ml based on the original cell count after harvest. The cells in the cell/PBS slurry were counted, and the density of cells in the suspension was adjusted to $50 \times 10^6$ cells/ml PBS. For each injection, a total of 0.15 ml of cell slurry was aspirated into a 1cc Glasspak syringe and the syringe was capped with a 22G/1 inch needle. The cell slurry was injected SC into the left side of the mouse, inferior and caudal to the ribs. Taking into consideration the void volume of the needle, a total of 0.1 ml, or $5 \times 10^6$ cells, was injected into each control animal (n=5 mice per condition).

Figure 5:
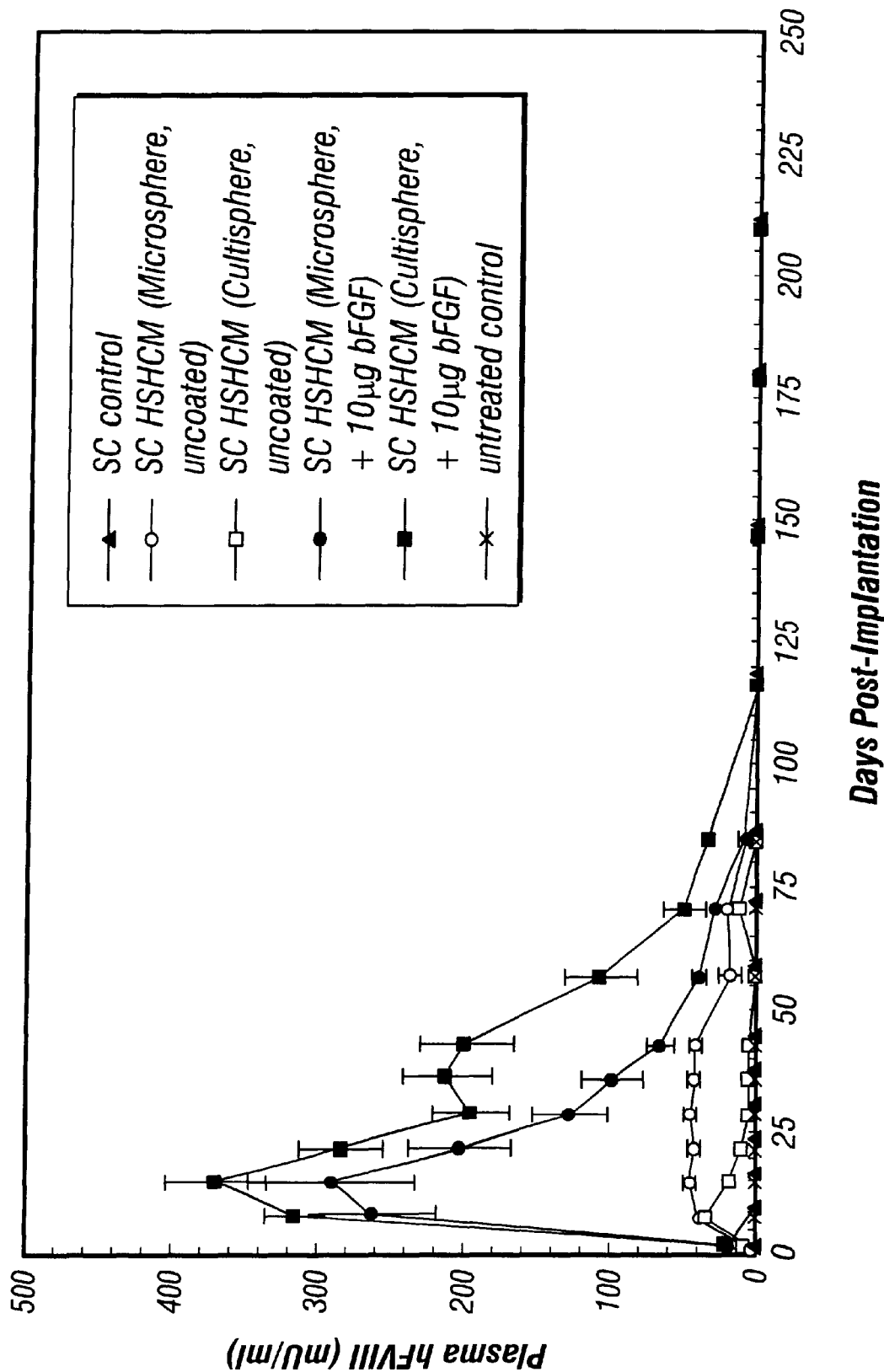
FIG. 5 is a line graph showing levels of hFVIII in plasma from mice implanted with HSHCM containing cells -a:: producing hFVIII, one of two types of microspheres, and heparin-Sepharose beads either coated with bFGF or uncoated.

FIG. 5 shows that the HSHCM containing the gelatin microspheres and bFGF-coated heparin-Sepharose beads led to a significantly higher level of hFVIII compared to the other conditions (n=10 mice per condition). The expression pattern was similar to that observed in Example XIII, with no detectable hFVIII until day 7, and highest expression at day 14. There was no detectable hFVIII in the plasma of the mice receiving SC cell injections at any time point after day 1 post-implantation.

EXAMPLE XV

HSHCM containing heparin-Sepharose beads either uncoated or coated with bFGF at 12.5, 25, or 50µg/ml packed beads were prepared using the collagen microsphere formulation (Table 8). The total amount of bFGF per matrix after incorporation of the coated beads was estimated to be approximately 2, 4, and 10 µg. The average number of cells per matrix and hFVIII production per matrix on the day of implantation (n 3 matrices per condition) are summarized in Table 11.

TABLE 11

Summary of cell number and hFVIII production per HSHCM on the day of implantation.

| Condition | Cell # (× $10^6$) | hFVIII (mU/24 h/HSHCM) |
|---|---|---|
| Uncoated heparin-Sepharose beads | 3.8 | 62,956 |

TABLE 11-continued

Summary of cell number and hFVIII production per HSHCM on the day of implantation.

| Condition | Cell # (× $10^6$) | hFVIII (mU/24 h/HSHCM) |
|---|---|---|
| bFGF at 2 µg/HSHCM | 7.0 | 92,836 |
| bFGF at 4 µg/HSHCM | 10.9 | 80,976 |
| bFGF at 10 µg/HSHCM | 8.2 | 97,964 |

Figure 6:
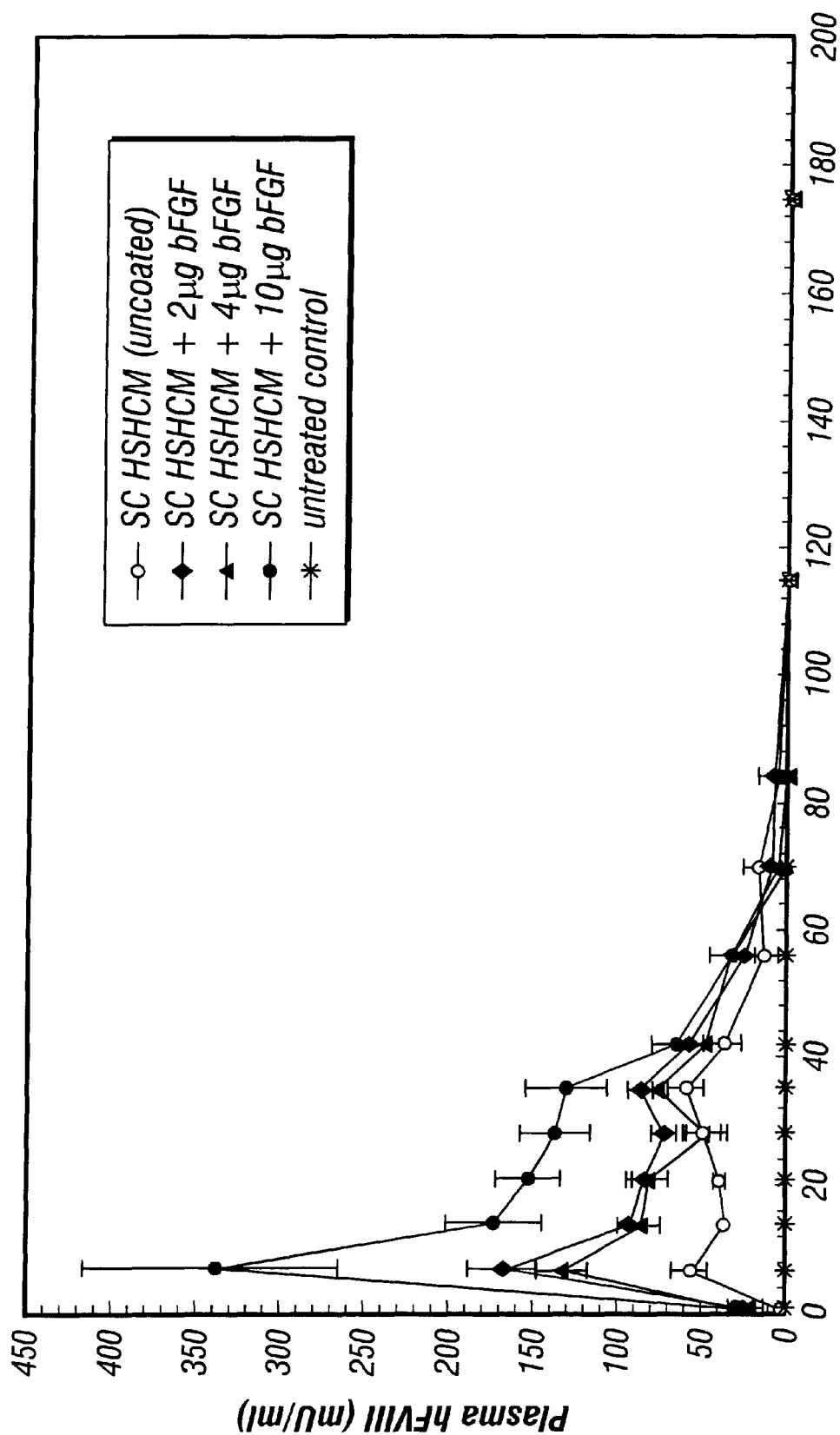
FIG. 6 is a line graph showing levels of hFVIII in plasma from mice implanted with HSHCM containing cells producing hFVIII and heparin-Sepharose beads coated with various concentrations of bFGF.

FIG. 6 demonstrates that plasma levels of HFVIII are significantly higher from matrices containing 10 µg of bFGF as compared to those containing 4 µg and 2 µg of bFGF (n=5 mice per condition). The pattern of expression was similar to that observed in Examples XIII and XIV.

EXAMPLE XVI

HSHCM containing heparin-Sepharose beads either uncoated, coated with bFGF, coated with VEGF, or coated with both bFGF and VEGF were prepared according to the gelatin microsphere formulation (Table 9). For the set of HSHCM containing beads coated with both growth factors, each matrix received 0.1 ml of beads coated with bFGF and 0.1 ml of beads coated with VEGF in order to keep the bead volume consistent with previous experiments. The coating concentration of each growth factor for this condition was 100 µg/ml packed beads, resulting in a total of approximately 10 µg of each growth factor per HSHCM. The average number of cells per matrix and hFVIII production per matrix on the day of implantation (n=3 matrices per condition) are summarized in Table 12.

TABLE 12

Summary of cell number and hFVIII production per HSHCM on the day of implantation.

| Condition | Cell # (× $10^6$) | hFVIII (mU/24 h/HSHCM) |
|---|---|---|
| Uncoated heparin-Sepharose beads | 3.7 | 101,048 |
| HSHCM + bFGF | 3.5 | 128,654 |
| HSHCM + VEGF | 3.4 | 76,152 |
| HSHCM + bFGF + VEGF | 4.9 | 127,450 |

Intraomental (IO) implantation controls were included in order to compare the subcutaneous delivery of hFVIII from HSHCM with another implantation method that has proven successful for the delivery of hFVIII in the mouse model. IO controls were prepared as follows. Cells were harvested by trypsinization in the same manner as for preparation of HCM. The trypsinized cells were counted, centrifuged at 500×g, resuspended in Hank's Buffered Saline Solution (without calcium and magnesium), recentrifuged, and resuspended in a volume of PBS to give $15 \times 10^6$ cells/ml based on the original cell count after harvest. The cells in the cell/PBS slurry were counted, and a volume of cell suspension equal to $5 \times 10^6$ cells was distributed into sterile 1.5 ml Eppendorf tubes and centrifuged at 500×g for 4 min in a microcentrifuge. The tubes containing the cell pellet and PBS were placed on ice, and each cell pellet was implanted into the omental recess of the Rag-2 mouse in the following manner. Prior to implantation of cells, mice were anesthetized with 1.25% Avertin and placed in lateral recumbency. The left flank between the ribs and stifle was wiped with an alcohol pad and prepped with Betadine. A small (0.5 cm to 1.0 cm) incision was made posterior to the ribs and ventral to the spine. The spleen was exposed and gently exteriorized. Cells were injected along the axis of the spleen upon the cranial and medial aspect and within the thin membrane adjacent to the hilar surface of the spleen. The spleen was replaced in the abdominal cavity, and the incision closed.

Figure 7:
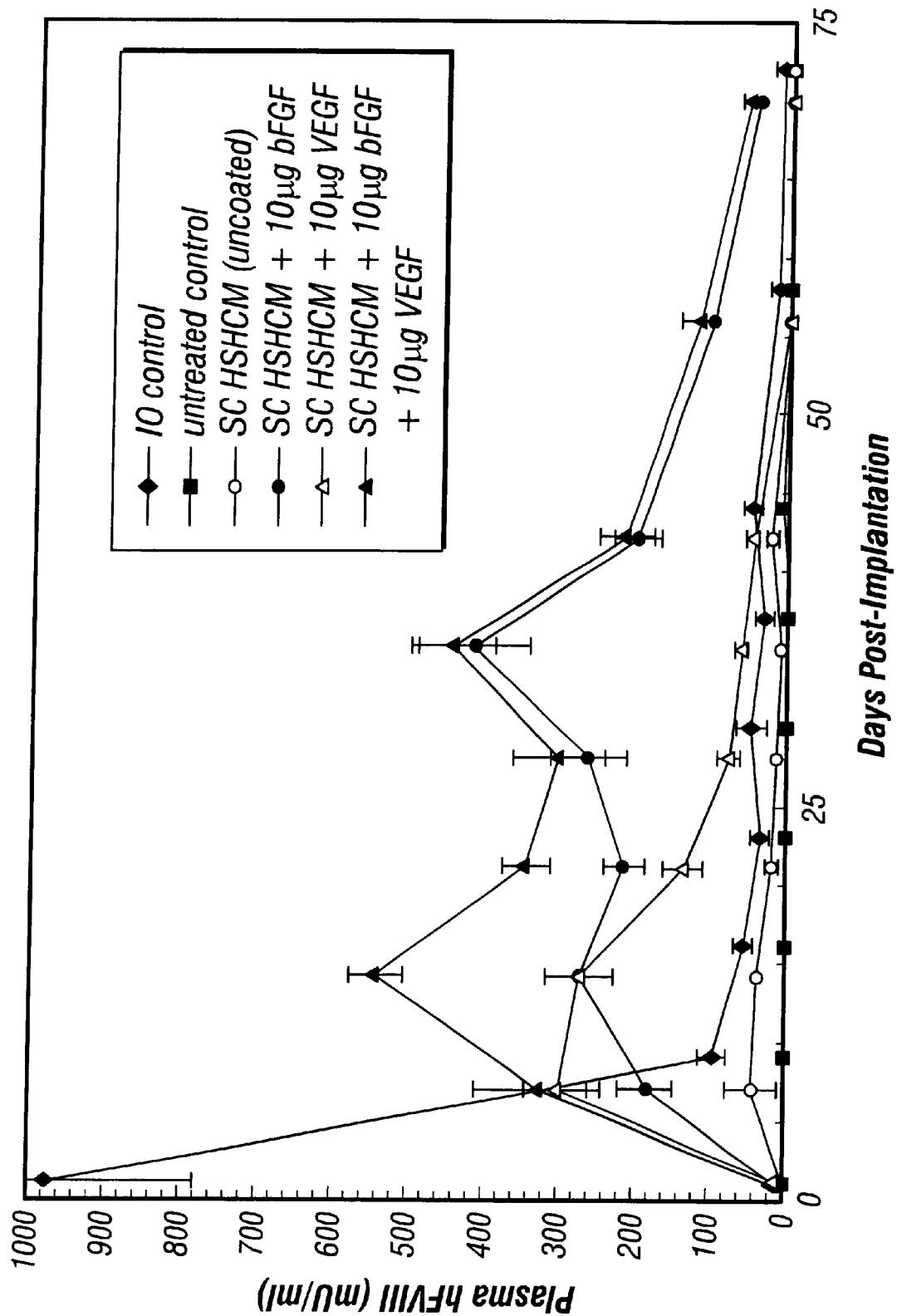
FIG. 7 is a line graph showing levels of hFVIII in plasma from mice implanted with HSHCM containing cells producing hFVIII and either heparin-Sepharose beads coated with bFGF, heparin-Sepharose beads coated with vascular endothelial growth factor (VEGF), or a mixture of heparin-Sepharose beads coated with bFGF and heparin-Sepharose beads coated with VEGF.

FIG. 7 demonstrates that the plasma hFVIII levels are significantly higher from HSHCM containing a combination of bFGF and VEGF as compared to the other conditions at days 14 and 21 (n=5 mice per condition). The injection of cells IO led to a significantly higher plasma hFVIII level on day 1, but by the next time point (day 7), the level observed in IO controls fell below that obtained with the HSHCM implants containing growth factors (n=5 mice per condition).

EXAMPLE XVII

Figure 8:
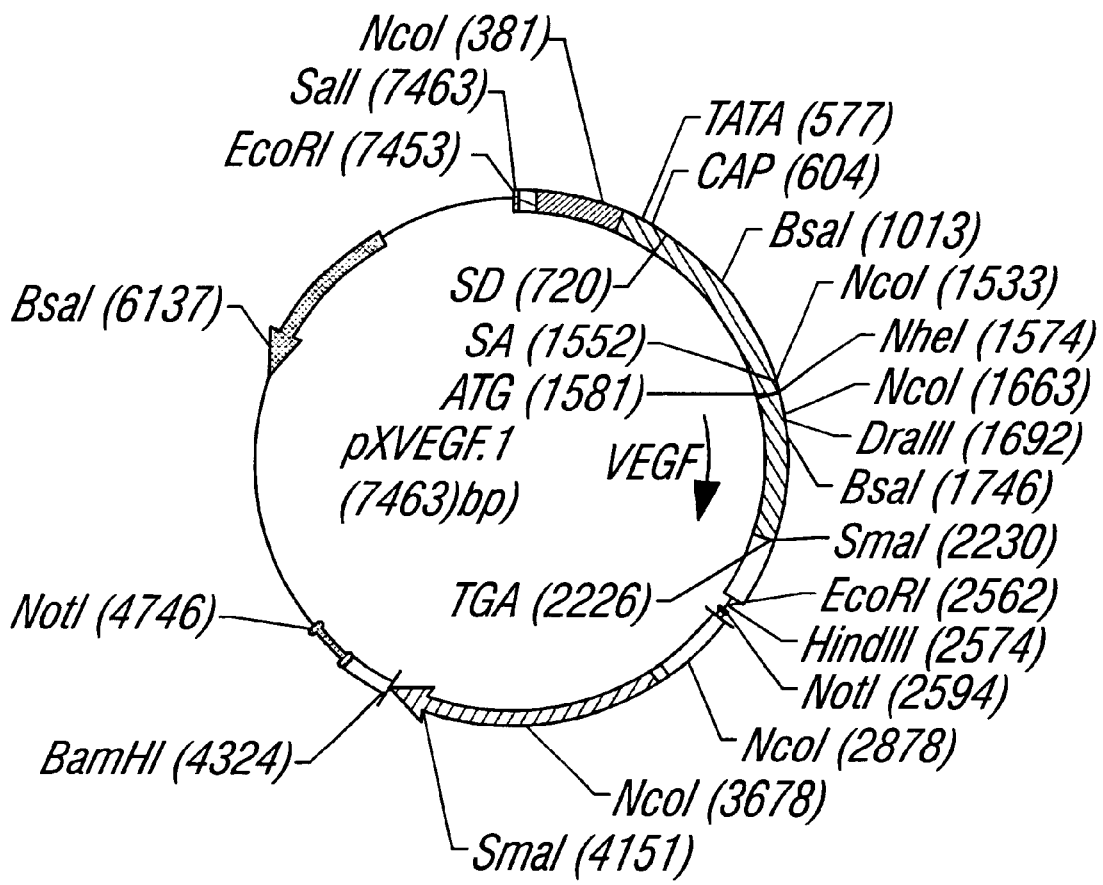
FIG. 8 is a diagram depicting the pXVEGF.1 plasmid.

HSHCM containing a combination of 2 fibroblast cell clones, HF743 B1-35 expressing hFVIII and HF811-M15 containing plasmid pXVEGF.1 (FIG. 8) and expressing VEGF [Kock et al., Science 246:1309–1312, 1989], were prepared for implantation. The HF811-M15 clone was producing an average of 85 ng VEGF/24 h/$10^6$ cells at the time of implantation. The matrices were prepared according to the collagen microsphere formulation (Table 8). The heparin-Sepharose bead component was uncoated. Two sets of HSHCM were prepared with one or the other clone at $5 \times 10^6$ cells per matrix. An additional two sets were prepared with a constant number of HF743 B1-35 cells ($5 \times 10^6$) and an additional $1 \times 10^6$ or $2.5 \times 10^6$ of HF811-M15 cells. Table 13 summarizes the different conditions and production levels of hFVIII and VEGF for each condition (n=5 matrices per condition).

TABLE 13

Summary of hFVIII and VEGF production per HSHCM on day of implantation.

| Condition (cells/matrix) | hFVIII (mU/24 h) | VEGF (ng/24 h) |
|---|---|---|
| HF743 B1-35 ($5 \times 10^6$) | 65,442 | n/a |
| HF743 B1-35 ($5 \times 10^6$) + HF811-M15 ($1 \times 10^6$) | 79,828 | 47 |
| HF743 B1-35 ($5 \times 10^6$) + HF811-M15 ($2.5 \times 10^6$) | 63,876 | 86 |
| HF811-M15 $5 \times 10^6$ | n/a | 82 |

Figure 9:
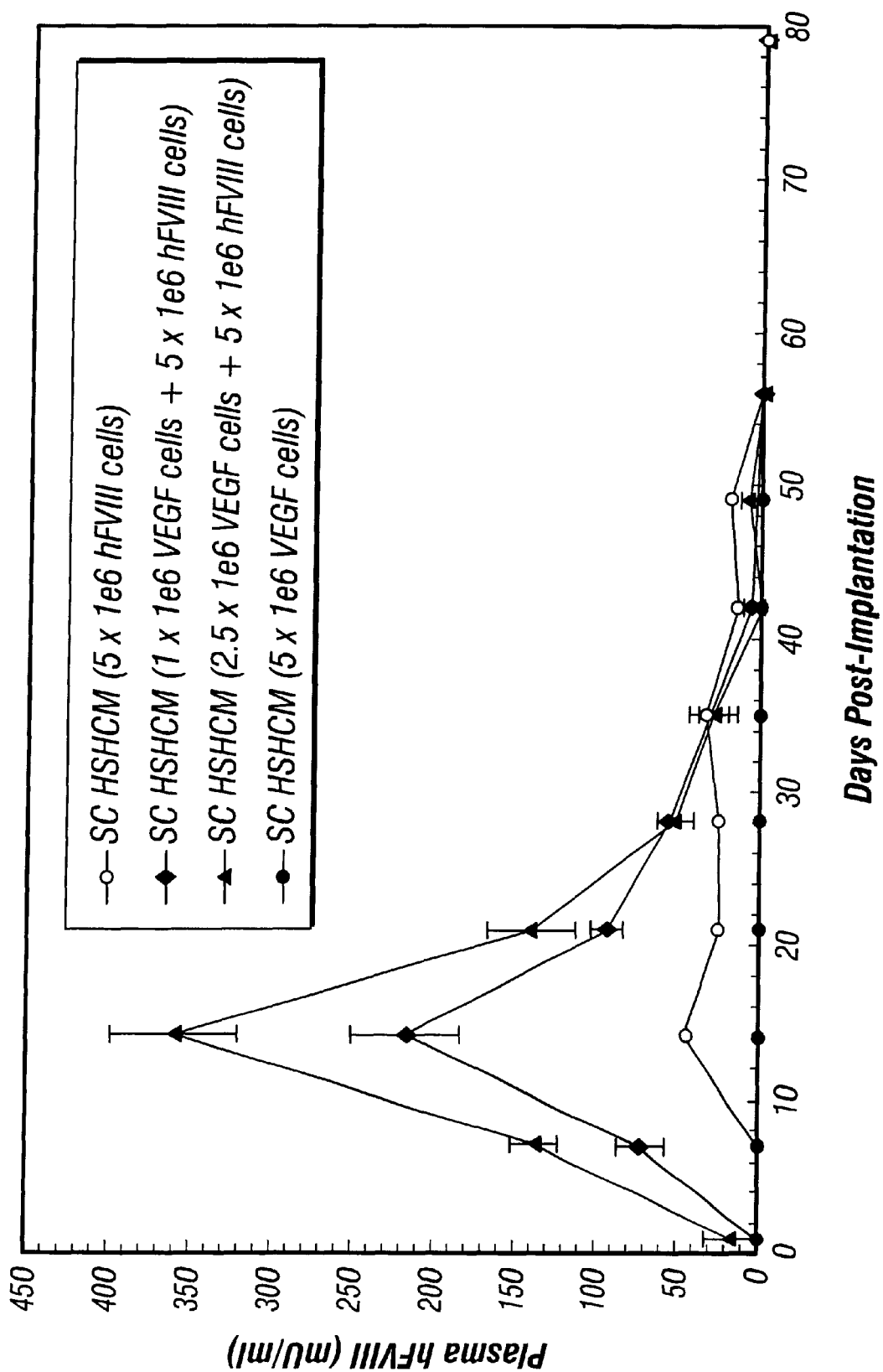
FIG. 9 is a line graph showing levels of hFVIII in plasma from mice implanted with HSHCM containing a first population of cells producing hFVIII, either alone or together with second population of cells producing VEGF.

Plasma hFVIII levels over time for each HSHCM condition are illustrated in FIG. 9. The set of HSHCM containing $2.5 \times 10^6$ HF811-M15 cells led to the highest hFVIII plasma levels, which peaked on day 14 and declined until day 42, at which time no hFVIII was detectable. The HSHCM containing $1 \times 10^6$ HF811-M15 cells led to plasma levels of hFVIII slightly lower than the set containing $2.5 \times 10^6$ HF811-M15, but significantly higher than the HSHCM without the VEGF-producing cells, indicating that VEGF produced a dose-dependent effect on the delivery of hFVIII by the implant.

The amount of VEGF in the plasma samples was determined by ELISA (R&D Systems VEGF Immunoassay Kit). The results are summarized in Table 14. There was a decline in detectable VEGF from day 14 to day 28 in plasma from mice implanted with HSHCM made with either $2.5 \times 10^6$ or $5 \times 10^6$ HF811-M15 cells. VEGF levels were not detectable in the plasma of animals implanted with HSHCM made without or with $1 \times 10^6$ HF811-M15 cells. Plasma samples for day 1 and 7 were not available for assay, but the data suggest that the VEGF level peaked at some point between time of implantation and day 14.

TABLE 14

Summary of VEGF expression in the plasma of Rag-2 mice implanted with HSHCM containing different numbers of HF811-M15 cells.

| Condition (cells/matrix) | Plasma VEGF (pg/ml) | | | |
|---|---|---|---|---|
| | Day 14 | Day 21 | Day 28 | Day 35 |
| HF743 B1-35 (5 × $10^6$) | 0 | 0 | 0 | 0 |
| HF743 B1-35 (5 × $10^6$) + HF811-M15 (1 × $10^6$) | 0 | 0 | 0 | 0 |
| HF743 B1-35 (5 × $10^6$) + HF811-M15 (2.5 × $10^6$) | 6.5 | 1.4 | 0 | 0 |
| HF811-M15 (5 × $10^6$) | 89 | 77 | 0 | 0 |

EXAMPLE XVIII

The volume of the mixture used to make the matrices of the invention is based on a liquid column height (i.e., depth) of 0.18 cm. A 4 ml volume of mixture in a 60 mm dish (radius 2.65 cm) was found to give optimal cell viability and protein expression for that size dish. Based on the formula $V=\pi r^2 h$, where V=volume of the mixture, r=radius of the dish, and h=height of the liquid column (i.e., depth of the mixture in the dish), the optimal volume of 4 ml=$\pi(2.65$ cm$)^2$h, so optimal depth=0.18 cm and optimal $r^2/V$ ratio= 1.8. The following table indicates optimal volumes for different dish sizes, including the 60 mm size from which the 0.18 cm height was derived.

TABLE 15

Optimal volumes and $r_2/V$ ratios for different size dishes.

| Dish Size (mm) | Diameter (cm) | Radius r (cm) | $r^2$ | Volume* (ml) | Ratio of $r^2$ to volume |
|---|---|---|---|---|---|
| 35 | 3.6 | 1.8 | 3.24 | 1.8 | 1.8 |
| 60 | 5.3 | 2.65 | 7.02 | 4 | 1.8 |
| 100 | 8 | 4 | 16 | 9 | 1.8 |
| 150 | 13.8 | 6.9 | 47.6 | 27 | 1.8 |

*based on equation: volume = $\pi\ r^2$ × 0.18 cm

While a ratio of about 1.8 was found to be optimal for cell viability and protein expression, ratios of about 1.0–3.0, preferably 1.5 to about 2.0, were adequate. These correspond to depths of about 0.21 cm and about 0.16 cm, respectively.

EXAMPLE XIX

Keratinocytes are epidermal cells of the skin, and are normally contiguous with fibroblasts in this tissue. These two cell types depend on one another for the proper nutrients, differentiation signals, and production and maintenance of surrounding extracellular matrix. The addition of keratinocytes to any of the hybrid collagen matrices described herein which contain fibroblasts can benefit the fibroblasts within the matrix in a manner similar to what occurs in the skin. The keratinocytes and fibroblasts can be isolated from the same skin biopsy. The keratinocytes can be added simultaneously with the fibroblasts at the time of matrix formation, or they can be seeded onto a contracted matrix containing fibroblasts. The keratinocytes within or on the matrix can be stimulated to differentiate, or not, depending upon the growth medium formulation and culture conditions. For example, an increase in the concentration of calcium ion in the growth medium, and the exposure of one side of the matrix to air, can cause the keratinocytes within the matrix to stratify in a manner similar to what occurs in the skin (Bell et al., J. Biomech. Eng. 113:113–119, 1991; Parenteau et al., J. Cell. Biochem. 45:245–251, 1991). Once differentiated, the keratinocytes lay down basal lamina consisting of collagen, glycosaminoglycans, and laminin. These basal lamina components as well as extracellular matrix proteins, which can be either synthesized by fibroblasts or included in the production medium, provide a physiological framework that is advantageous to fibroblast survival, e.g., after implantation of the matrix in a subject.

EXAMPLE XX

Endothelial cells form the lumen of blood vessels and capillaries. Vessels are formed from single endothelial cells that divide and differentiate to form contiguous tubes. This differentiation process can be stimulated in an in vitro setting in the presence of essential environmental factors. These factors include collagen, extracellular matrix proteins produced by cells such as fibroblasts and/or keratinocytes, and growth factors (e.g., basic fibroblast growth factor or vascular endothelial growth factor). The hybrid collagen matrices described herein can provide the proper environment for endothelial tube formation if endothelial cells are added to the matrix production medium along with fibroblasts. The addition of keratinocytes can help induce differentiation of the endothelial cells through secretion of factors such as vascular endothelial growth factor as well as production of a basal lamina. The formation of endothelial tubes within the hybrid matrix can accelerate the vascularization of the hybrid collagen matrix after implantation by inosculation of the pre-existing endothelial tubes with the growing blood vessels of the host (Black et al., FASEB J. 12:1331–1340, 1998; Black et al., Cell Biol. Toxicol. 15(2):81–90, 1999).

Other Embodiments

The hybrid matrices of the invention are appropriate for delivery of a wide range of cellular products, including not only hGH and Factor VIII, but also Factor IX, erythropoietin (EPO), albumin, hemoglobin, alpha-1 antitrypsin, calcitonin, glucocerebrosidase, low density lipoprotein (LDL) receptor, IL-2 receptor, globin, immunoglobulin, catalytic antibodies, the interleukins, insulin, insulin-like growth factor 1 (IGF-1), insulinotropin, parathyroid hormone (PTH), leptin, an IFN (e.g., IFN-α, IFN-β, or IFN-γ), the nerve growth factors, basic fibroblast growth factor (bFGF), acidic FGF (aFGF), epidermal growth factor (EGF), endothelial cell growth factor, platelet derived growth factor (PDGF), transforming growth factors, endothelial cell stimulating angiogenesis factor (ESAF), angiogenin, tissue plasminogen activator (t-PA), granulocyte colony stimulating factor (G-CSF), granulocyte-macrophage colony stimulating factor (GM-CSF), α-galactosidase, and FSH. For example, the cells embedded in the matrix can be pancreatic beta cells which naturally secrete insulin in response to a rise in blood glucose, and which therefore can supplement an inadequate insulin response in a diabetic or pre-diabetic patient. Alternatively, they can be any type of cell genetically engineered to express and secrete high levels of a needed polypeptide, such as a clotting factor, within the patient. Such a construct may be under the control of a constitutively activated promoter, or of an appropriately physiologically or pharmacologically regulated promoter.

The collagen gel portion of the matrix can consist entirely of insoluble collagen fibrils, or can contain other components in addition to collagen: e.g., agarose; alginate; a glycosaminoglycan such as hyaluronic acid, heparin sulfate, dermatan sulfate, or chondroitin sulfate; a sulfated proteoglycan; fibronectin; laminin; elastin; fibrin; or tenascin. Such components (particularly those which are found in the extracellular matrix of animal tissues) contribute to the structural stability of the hybrid matrices of the invention, and/or provide additional attachment capacity for the cells in the matrices and the host tissue at the site of implantation. They would be incorporated into the matrices by mixing with the collagen solution prior to gelling.

Other potential additives include cytokines and/or growth factors which are useful for optimizing maintenance of the cells or promoting beneficial interaction with host tissue (e.g., vascularization), including bFGF, aFGF, endothelial cell growth factor, PDGF, endothelial cell stimulating angiogenesis factor (ESAF), leukotriene $C_4$, prostaglandins (e.g., $PGE_1$, $PGE_2$), IGF-1, GCSF, angiogenin, TGF-$\alpha$, TGF-$\beta$, ascorbic acid, EGF, oncostatin M, VEGF, VEGF-A, VEGF-B, VEGF-C, and VEGF-D. These additives can be incorporated into the matrix by mixing them with the collagen solution prior to gelling, by introducing them into the interstices of the microspheres, or by including them in the medium which bathes the matrices. They can also be bound to or encapsulated within separate solid substrates (e.g., heparin-coated agarose beads or PLGA microcapsules) included in the matrices. Alternatively, the cells may be genetically engineered to express the desired product. For example, the cells of the matrix may be cotransfected with a DNA encoding an angiogenesis factor and a DNA encoding a second, therapeutic protein, or with a single DNA construct encoding both types of proteins linked to suitable expression control sequences.

Ascorbic acid promotes the production of mature collagen by fibroblasts by promoting the proper post-translational modification of procollagen. The production of collagen by fibroblasts embedded within the hybrid collagen matrix will increase the physical strength of the matrix as well as provide a physiological architecture that may increase cell survival once implanted.

The collagen used in the gel may be any suitable type (e.g., type I–XI), or a mixture of any two or more. Fibers may be placed in the mold prior to gelling of the collagen, so that they become an integral part of the matrix and contribute to the sturdiness and handling convenience of the matrix. Typically, the fibers would be made principally of collagen (e.g., cat gut) or a non-collagenous material such as nylon, dacron, polytetrafluoroethylene (Gore-Tex™ or Teflon™), polyglycolic acid, polylactic/polyglycolic acid mixture (Vicryl™), polystyrene, polyvinylchloride co-polymer, cellulose (e.g., cotton or linen), polyester, rayon, or silk. The fibers may be woven into a mesh or cloth, or used as individual threads.

Instead of the type I collagen microspheres described in the above examples, one could utilize microspheres consisting primarily of another type of collagen, polystyrene, dextran (e.g., Cytodex™, Pharmacia), polyacrylamide, cellulose, calcium alginate, latex, polysulfone, glass (coated with a substance such as collagen which promotes cellular adherence), gelatin, or combinations of collagen with any of the above. Such microspheres are available commercially or can be made by standard methods, then sterilized for use in the hybrid matrices of the invention.

Other embodiments are within the following claims.

What is claimed is:

1. A composition comprising a body of matrix material comprising insoluble collagen fibrils, there being embedded within the body of matrix material
   (a) a population of cultured vertebrate cells genetically engineered to express a polypeptide;
   (b) a plurality of microspheres; and
   (c) an agent selected from the group consisting of a factor which promotes vascularization, a cytokine, a growth factor and ascorbic acid.

2. The composition of claim 1, wherein the agent is associated with a solid substrate embedded in the body of the matrix material.

3. The composition of claim 2, wherein the solid substrate comprises heparin or heparan sulfate proteoglycan.

4. The composition of claim 2, wherein the solid substrate comprises agarose with hepain or heparan sulfate proteoglycan bound thereto.

5. The composition of claim 4, wherein the solid substrate further comprises calcium alginate.

6. The composition of claim 2, wherein the solid substrate further comprises calcium alginate.

7. The composition of claim 2 wherein the solid substrate comprises a substance selected from the group consisting of collagen, gelatin, ethylene-vinyl acetate, polylactide/glycolic acid co-polymer, fibrin, sucrose octasulfate, dextran, polyethylene glycol, an alginate, polyacrylamide, cellulose, latex, and polyhydroxyethylmethacrylate.

8. The composition of claim 7, wherein heparin or heparan sulfate proteoglycan is bound to the substance.

9. The composition of claim 1, wherein the composition further comprises a second agent selected from the group consisting of a factor which promotes vascularization, a cytokine, and a growth factor.

10. The composition of claim 2, wherein the solid substrate is in the form of beads.

11. The composition of claim 2, wherein the solid substrate is in the form of threads.

12. The composition of claim 1, wherein the agent is basic fibroblast growth factor (bFGF).

13. The composition of claim 1, wherein the agent is selected from the group consisting of acidic fibroblast growth factor (aFGF), endothelial cell growth factor, platelet-derived growth factor (PDGF), endothelial cell stimulating angiogenesis factor (ESAF), leukotriene $C_4$, a prostaglandin, insulin-like growth factor 1 (IGF-1), granulocyte colony stimulating factor (G-CSF), angiogenin, transforming growth factor-$\alpha$ (TGF-$\alpha$), transforming growth factory-$\beta$ (TGF-$\beta$), ascorbic acid, epidermal growth factor (EGF), and oncostatin M.

14. The composition of claim 1, wherein the agent is selected from the group consisting of vascular endothelial growth factor (VEGF), VEGF-A, VEGF-B, VEGF-C, and VEGF-D.

15. The composition of claim 1, wherein the cultured vertebrate cells are selected from the group consisting of adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, pancreatic beta cells, renal cells, smooth muscle cells, striated muscle cells, and precursors of any of the above.

16. The composition of claim 1, wherein the cultured vertebrate cells are human cells.

17. The composition of claim 1, wherein the polypeptide is selected from the group consisting of enzymes, hormones, cytokines, colony stimulating factors, vaccine antigens, antibodies, clotting factors, regulatory proteins, transcription factors, receptors, and structural proteins.

18. The composition of claim 1, wherein the polypeptide is Factor VIII.

19. The composition of claim 1, wherein the polypeptide is human growth hormone.

20. The composition of claim 1, wherein the polypeptide is Factor IX.

21. The composition of claim 1, wherein the polypeptide is erythropoietin.

22. The composition of claim 1, wherein the polypeptide is selected from the group consisting of VEGF, VEGF-A, VEGF-B, VEGF-C, and VEGF-D.

23. The composition of claim 1, wherein the polypeptide is insulinotropin.

24. The composition of claim 1, wherein the polypeptide is selected from the group consisting of alpha-1 antitrypsin, calcitonin, glucocerebrosidase, low density lipoprotein (LDL) receptor, IL-2 receptor, globin, immunoglobulin, catalytic antibodies, the interleukins, insulin, insulin-like growth factor 1 (IGF-1), parathyroid hormone (PTH), leptin, the nerve growth factors, basic fibroblast growth factor (bFGF), acidic FGF (aFGF), epidermal growth factor (EGF), endothelial cell growth factor, platelet derived growth factor (PDGF), transforming growth factors, endothelial cell stimulating angiogenesis factor (ESAF), angiogenin, tissue plasminogen activator (t-PA), granulocyte colony stimulating factor (G-CSF), and granulocyte-macrophage colony stimulating factor (GM-CSF).

25. The composition of claim 1, wherein the microspheres are beads of type I collagen.

26. The composition of claim 25, wherein the microspheres are porous.

27. The composition of claim 1, wherein the microspheres are beads of porous gelatin.

28. The composition of claim 1, wherein the majority of the microspheres have an approximately spherical shape and have a diameter between approximately 0.1 and approximately 2 mm.

29. The composition of claim 1, wherein the matrix material additionally comprises a substance selected from the group consisting of a second type of collagen, agarose, alginate, fibronectin, laminin, hyaluronic acid, heparan sulfate, dermatan sulfate, sulfated proteoglycans, fibrin, elastin, and tenascin.

30. The composition of claim 1, additionally comprising noncollagen fibers dispersed within the body of matrix material.

31. The composition of claim 30, wherein the noncollagen fibers comprise a material, selected from the group consisting of nylon, dacron, polytetrafluoroethylene, polyglycolic acid, polylactic/polyglycolic acid copolymer, polystyrene, polyvinylchloride, cat gut, cotton, linen, polyester, and silk.

32. The composition of claim 1, configured to be implanted into a patient.

33. The composition of claim 32, wherein the cultured vertebrate cells are derived from one or more cells removed from the patient.

34. The composition of claim 33, wherein the cultured vertebrate cells consist of a clonal population.

35. The composition of claim 1, wherein each of the plurality of microspheres consists primarily of one or more substances selected from the group consisting of collagen, polystyrene, dextran, polyacrylamide, cellulose, calcium alginate, latex, polysulfone, and glass.

36. The composition of claim 1, wherein the cultured vertebrate cells are fibroblasts.

37. The composition of claim 1, wherein the microspheres have an approximately spherical shape.

38. A method of making the composition of claim 1, comprising
    forming a mixture comprising:
    (a) a plurality of cultured vertebrate cells genetically engineered to express a polypeptide;
    (b) a plurality of microspheres;
    (c) a solution comprising soluble collagen; and
    (d) an agent selected from the group consisting of a factor that promotes vascularization, a cytokine, a growth factor, and ascorbic acid;
    subjecting the soluble collagen in the mixture to conditions effective to form a gel; and
    exposing the gel to culture conditions which cause the gel to contract, thereby forming the body of the composition.

39. The method of claim 38, wherein the agent is associated with a solid substrate.

40. The method of claim 39, wherein the solid substrate comprises beads of agarose with heparin or heparan sulfate proteoglycan bound thereto.

41. The method of claim 39, wherein the solid substrate further comprises calcium alginate.

42. The method of claim 40, wherein the solid substrate comprises calcium alginate.

43. The method of claim 39, wherein the solid substrate comprises a substance selected from the group consisting of collagen, gelatin, ethylene-vinyl acetate, polylactide/glycolic acid co-polymer, fibrin, sucrose octasulfate, dextran, polyethylene glycol, an alginate, polyacrylamide, cellulose, latex, and polyhydroxyethylmethacrylate.

44. The method of claim 43, wherein heparin or heparan sulfate proteoglycan is bound to the substance.

45. The method of claim 38, wherein the microspheres are porous collagen beads.

46. The method of claim 38, wherein the microspheres are porous gelatin beads.

47. The method of claim 38, wherein the mixture additionally comprises a substance selected from the group consisting of a second type of collagen, agarose, alginate, fibronectin, laminin, hyaluronic acid, heparan sulfate, dermatan sulfate, sulfated proteoglycans, fibrin, elastin, and tenascin.

48. The method of claim 38, wherein the solution is an acidic aqueous solution of soluble collagen, and gelation is accomplished by raising the pH of the solution.

49. The method of claim 38, wherein the gelation step takes place in a mold, so that, prior to the contracting step, the gel is in the shape of the mold.

50. The method of claim 38, wherein the cultured vertebrate cells are cultured in the presence of the microspheres prior to being mixed with the solution.

51. A method of administering a polypeptide to a patient in need thereof, comprising
    providing the composition of claim 32, wherein the cultured vertebrate cells secrete the polypeptide; and
    implanting the composition in the patient, wherein the cultured vertebrate cells secrete the polypeptide after implanting the composition in the patient.

52. The method of claim 51, wherein the cultured vertebrate cells are derived from one or more cells removed from the patient, and have been genetically engineered in vitro to express and secrete the polypeptide.

53. The method of claim 51, wherein the implanting is carried out at a subcutaneous site in the patient.

54. The method of claim 51, wherein the implanting is carried out at an intraperitoneal, sub-renal capsular, inguinal, intramuscular, intraventricular, intraomental, or intrathecal site in the patient.

55. The method of claim 51, wherein the polypeptide is one which promotes wound healing, and the implanting is carried out at the site of a preexisting wound of the patient.

56. The method of claim 51, wherein each of the plurality of microspheres consists primarily of one or more substances selected from the group consisting of collagen, polystyrene, dextran, polyacrylamide, cellulose, calcium alginate, latex, polysulfone, and glass.

57. The method of claim 51, wherein each of the plurality of microspheres consists primarily of gelatin.

58. The method of claim 38, wherein the gel is formed in a flat-bottomed mold filled with the mixture to a depth of about 0.18 cm.

59. A composition produced by the method of claim 58.

60. The method of claim 38, wherein the gel is formed in a flat-bottomed cylindrical mold with an internal radius (r); the mixture has a volume (V); and when r is expressed in cm and V is expressed in ml, $r^2/V$ is about 1.8.

61. A method of making a composition, the method comprising
    forming a mixture comprising:
        (a) a plurality of cultured vertebrate cells genetically engineered to express a polypeptide;
        (b) a plurality of microspheres; and
        (c) a solution comprising soluble collagen;
    subjecting the soluble collagen in the mixture to conditions effective to form a gel; and
    exposing the gel to culture conditions which cause the gel to contract, thereby forming the body of the composition,
    wherein the gel is formed in a flat-bottomed mold filled with the mixture to a depth of about 0.18 cm.

62. A composition produced by the method of claim 61.

63. A method of making a composition, the method comprising
    forming a mixture comprising:
        (a) a plurality of cultured vertebrate cells genetically engineered to express a polypeptide;
        (b) a plurality of microspheres; and
        (c) a solution comprising soluble collagen;
    subjecting the soluble collagen in the mixture to conditions effective to form a gel; and
    exposing the gel to culture conditions which cause the gel to contract, thereby forming the body of the composition,
    wherein the gel is formed in a flat-bottomed cylindrical mold with an internal radius (r); the mixture has a volume (V); and when r is expressed in cm and V is expressed in ml, $r^2/V$ is about 1.8.

64. The composition of claim 1, wherein the polypeptide is selected from the group consisting of interferon-α (IFN-α), interferon-β (IFN-β), interferon-γ (IFN-γ), follicle stimulating hormone (FSH), α-galactosidase, β-gluceramidase, α-iduronidase, α-L-iduronidase, glucosamine-N-sulfatase, α-N-acetylglucosaminidase, acetylcoenzyme A:α-glucosaminide-N-acetyltransferase, N-acetylglucosamine-6-sulfatase, β-galactosidase, N-acetylgalactosamine-6-sulfatase, and β-glucuronidase.

65. The composition of claim 1, wherein the matrix material additionally comprises a substance selected from the group consisting of heparin, cellulose, starch and dextran.

66. The method of claim 38, wherein the mixture additionally comprises a substance selected from the group consisting of heparin, cellulose, starch, and dextran.

* * * * *

UNITED STATES PATENT AND TRADEMARK OFFICE
CERTIFICATE OF CORRECTION

PATENT NO. : 6,419,920 B1
DATED : July 16, 2002
INVENTOR(S) : Rochelle Mineau-Hanschke It is certified that error appears in the above-identified patent and that said Letters Patent is hereby corrected as shown below:

Title page,
Item [73], Assignee, "Trans Karyotic Therapies, Inc." should read as
-- Transkaryotic Therapies, Inc. --.
Item [56], References Cited, OTHER PUBLICATIONS,
"Substrate" should read as -- Substrata --.
"Potent" should read as -- Potential --.
"morphogenic" should read as -- morphogenetic --.
"Biogen." should read as -- Bioeng. --.

Column 1,
Line 34, delete "," after "produce".

Column 8,
Line 39, delete "-a::" after "cells".

Column 13,
Line 26, "Ag/ml" should read as -- µg/ml --.
Line 43, "TGF-0" should read as -- TGFβ --.

Column 16,
Line 60, "(-0.1" should read as -- (~0.1 --.

Column 18,
Line 2, "+standard" should read as -- ±standard --.
Line 32, "Ag" should read as -- µg --.

Column 19,
Line 23, "ug" should read as -- µg --.

Column 22,
Line 48, "GLt™" should read as -- GL™ --.

Column 23,
Line 49, "iN" should read as -- 1N --.

Column 26,
Line 56, "(n 3" should read as -- (n=3 --.

UNITED STATES PATENT AND TRADEMARK OFFICE
CERTIFICATE OF CORRECTION

PATENT NO. : 6,419,920 B1
DATED : July 16, 2002
INVENTOR(S) : Rochelle Mineau-Hanschke It is certified that error appears in the above-identified patent and that said Letters Patent is hereby corrected as shown below:

Column 27,
Line 12, "HFVIII" should read as -- hFVIII --.

Column 32,
Line 21, "hepain" should read as -- heparin --.

Signed and Sealed this

Twenty-eighth Day of January, 2003

JAMES E. ROGAN
*Director of the United States Patent and Trademark Office*